US012752017B2

(12) United States Patent
Kent et al.

(10) Patent No.: US 12,752,017 B2
(45) Date of Patent: Oct. 6, 2026

(54) THERAPEUTIC CARBON NANOMATERIAL $H_2S$ OXIDANTS FOR BIOLOGICAL POLYSULFIDE SYNTHESIS

(71) Applicants: The Texas A&M University System, College Station, TX (US); William Marsh Rice University, Houston, TX (US); The Trustees of Indiana University, Bloomington, IN (US)

(72) Inventors: Thomas A. Kent, Houston, TX (US); Paul J. Derry, Houston, TX (US); David P. Huston, Houston, TX (US); Anton V. Liopo, Houston, TX (US); James M. Tour, Bellaire, TX (US); Emily A. McHugh, Houston, TX (US); Kimberly Mendoza, Houston, TX (US); Kenneth R. Olson, Berrien Springs, MI (US); Mansoor Kahn, Houston, TX (US); William Sikkema, Langley, CA (US)

(73) Assignees: The Texas A&M University System; William Marsh Rice University; The Trustees of Indiana University

( * ) Notice: Subject to any disclaimer, the term of this patent is extended or adjusted under 35 U.S.C. 154(b) by 521 days.

(21) Appl. No.: 18/008,837

(22) PCT Filed: Jun. 7, 2021

(86) PCT No.: PCT/US2021/036232

§ 371 (c)(1),
(2) Date: Dec. 7, 2022

(87) PCT Pub. No.: WO2021/252382

PCT Pub. Date: Dec. 16, 2021

(65) Prior Publication Data

US 2023/0241245 A1 Aug. 3, 2023

Related U.S. Application Data

(60) Provisional application No. 63/036,351, filed on Jun. 8, 2020.

(51) Int. Cl.

| | |
|---|---|
| ***A61K 47/69*** | (2017.01) |
| ***A61K 9/00*** | (2006.01) |
| ***A61K 9/51*** | (2006.01) |
| ***A61K 47/60*** | (2017.01) |

(52) U.S. Cl.

CPC ............ *A61K 47/6929* (2017.08); *A61K 9/51* (2013.01); *A61K 47/60* (2017.08)

(58) Field of Classification Search

CPC ...... A61K 47/6929; A61K 9/51; A61K 47/60; A61K 9/0019

See application file for complete search history.

(56) References Cited

U.S. PATENT DOCUMENTS

| | | | | |
|---|---|---|---|---|
| 5,605,674 | A | 2/1997 | Purewal et al. | |
| 6,358,530 | B1 | 3/2002 | Eljamal et al. | |
| 6,509,006 | B1 | 1/2003 | Platz et al. | |
| 6,592,904 | B2 | 7/2003 | Platz et al. | |
| 7,097,827 | B2 | 8/2006 | Platz et al. | |
| 9,572,834 | B2 | 2/2017 | Tour et al. | |
| 10,520,509 | B2 | 12/2019 | Xian et al. | |
| 2014/0120081 | A1 * | 5/2014 | Tour ...................... | A61K 47/60 424/130.1 |

FOREIGN PATENT DOCUMENTS

| | | | |
|---|---|---|---|
| CN | 105832767 | * | 8/2016 |
| CN | 105832767 | A | 8/2016 |
| CN | 108310392 | * | 7/2018 |
| CN | 108310392 | A | 7/2018 |
| EP | 1428793 | A1 | 6/2004 |
| WO | 2017123820 | A1 | 7/2017 |

OTHER PUBLICATIONS

International Preliminary Report on Patentability re application No. PCT/US2021/036232, issuance date Dec. 13, 2022 (including written opinion of Sep. 27, 2021) 5 pages.

Kashfi, K. et al., "Biology and therapeutic potential of hydrogen sulfide and hydrogen sulfide-releasing chimeras," Biochemical pharmacology, (2013), vol. 85, No. 5, doi:10.1016/j.bcp.2012.10.019, pp. 689-703, XP028969114.1-21 * abstract; p. 690, left column * DOI: http://dx.doi.org/10.1016/j.bcp.2012.10.019.

Bandosz, T.J. et al., "On the Adsorption/Oxidation of Hydrogen Sulfide on Activated Carbons at Ambient Temperatures," Journal of Colloid and Interface Science, 246, 1-20 (2002); doi:10.1006/jcis.2001.7952.

Panagaki, T. et al., "Overproduction of Hydrogen Sulfide, Generated by Cystathionine βsynthase, Disrupts Brain Wave Patterns and Contributes to Neurobehavioral Dysfunction in a Rat Model of Down Syndrome," Redox Biology, vol. 51, May 2022, 102233; https://doi.org/10.1016/j.redox.2022.102233.

(Continued)

*Primary Examiner* — Mina Haghighatian

(74) *Attorney, Agent, or Firm* — Meunier Carlin & Curfman LLC

(57) ABSTRACT

A therapeutic method for catalytically forming persulfide and/or polysulfide from hydrogen sulfide in vitro and in vivo using endogenously or exogenously released hydrogen sulfide is disclosed. That method comprises contacting cells in need including those under oxidative stress, traumatic brain injury (TBI) and hypoxia, or have an excess of hydrogen sulfide or deficiency of protein persulfidation with oxidized carbon nanoparticulate material in which the particles contain a plurality of carbonyl, hydroxyl and carboxyl substituents. Oxidized carbon nanoparticulate (OCN) material can be prepared from any of a variety of sources of which activated charcoal is preferred. A water-dispersible OCN material is described that does not need added hydrophilic polymers to provide dispersibility for at least 7 days at a concentration of about 1-5 mg/mL. These OCN materials also have a UV absorbance maximum in water of about 220 nm and pass through a 0.22 μm pore PES membrane.

17 Claims, 22 Drawing Sheets

(56) References Cited

OTHER PUBLICATIONS

Extended European Search Report re application No. EP 21822854.2, dated Nov. 10, 2023.
Samuel, E.L.G. et al., "Hydrophilic Carbon Clusters as Therapeutic, High Capacity Antioxidants," Trends Biotechnol. vol. 32, No. 10, Aug. 28, 2014, pp. 501-505. DOI: 10.1016/j.tibtech.2014.08.005. Epub Aug. 28, 2014. PMID: 25175886; PMCID: PMC4174960.

* cited by examiner

AC OAC PEG-OAC

THERAPEUTIC CARBON NANOMATERIAL $H_2S$ OXIDANTS FOR BIOLOGICAL POLYSULFIDE SYNTHESIS

STATEMENT REGARDING FEDERALLY SPONSORED RESEARCH OR DEVELOPMENT

This invention was made with government support under grant number R01 439371-00001 awarded by the National Institutes of Health. The government has certain rights in the invention.

FIELD OF THE INVENTION

The present invention relates to the field of carbon nanomaterials and to therapeutic uses thereof.

DESCRIPTION OF RELATED ART

Hydrogen sulfide ($H_2S$) is a gaseous material with several endogenous actions analogous to nitric oxide and carbon monoxide. It is a good reductant (readily oxidized) and attempts to employ it as a therapeutic have been made in the past. However, these attempts have been stymied by the inherent difficulties working with $H_2S$ gas, or its sulfide salts. In the former case, $H_2S$ is flammable and highly noxious with potential for toxicity. As a salt, sulfide salts decompose quickly limiting their therapeutic utility.

Attempts to resolve these shortcomings include the use of $H_2S$ donors to systemically circulate and release $H_2S$. However, although a donor can mitigate difficulties inherent in $H_2S$ as a gas or salt, it does not relieve the narrow therapeutic index and to date we are aware of only one clinical trial that has been completed using an $H_2S$ donor, N-acetylcysteine, an agent with other mechanisms of action.

$H_2S$ is metabolized to polysulfides in cells. Polysulfides are excellent reductants and have many potentially favorable actions with regard to oxidative stress. Polysulfides ($Na_xS_y$), derived from the oxidation of hydrogen sulfide, are efficacious antioxidants in vitro.

Polysulfides can be good reductants due to their weak terminal S—H bond. Polysulfides target both single and double electron oxidizers including superoxide and hydrogen peroxide (90, 92). In the case of two electron oxidizers, polysulfides appear to react faster than thiols such as glutathione and therefore may be a consequential component of the cellular antioxidant network (90, 92).

Generation of polysulfides acting as reductants is not the only consequence of metabolism of hydrogen sulfide that has biological importance. Proteinaceous persulfides (R—S—$S^-$), where R is a protein or polypeptide, have recently been identified as products of $H_2S$-based signaling and thereby influence a large number of protein functions with implications for a large number of biological processes and disease states.

Natively, polysulfides can be generated in cells by several enzymatic routes such as the catalytic oxidation of hydrogen sulfide by superoxide dismutase (87), catalase (91), cystathionine B-synthase (CBS) (89), and cysteinyl-tRNA synthetase (CARS) (89, 88). In addition, polysulfides can be formed by free-radical oxidation of hydrogen sulfide to form HS· after which reacts with itself ($H_2O+2HS\cdot \rightarrow HSS^- + H_3O^+$) or endogenous thiols (R—SH) to form R—SSH species (92).

Therefore, a means to rapidly generate polysulfides from $H_2S$ therefore holds therapeutic promise of overcoming limitations of administering $H_2S$ itself.

Another fate of polysulfides is their oxidation to thiosulfate ($S_2O_3^{2-}$) either through enzymatic, by way of hemeproteins, or nonenzymatic oxidation [Vitvitsky et al., *J Biol Chem* 2015; 290(13):8310-8320] from simple oxidation. Thiosulfate can serve as an $H_2S$ donor and has protective properties in ischemia reperfusion injury [Marutani et al., *J Am Heart Assoc* 2015; 4(11); Epub 2015 Nov. 8]. Otherwise, $S_2O_3^{2-}$ can also undergo further enzymatic oxidation in mitochondria to form sulfite ($SO_3^{2-}$) or sulfate ($SO_4^{2-}$) [Mishanina et al., *Nat Chem Biol* 2015; 11(7):457-464] where it is excreted from the body.

Oxidized carbon can be utilized to catalyze the oxidation of hydrogen sulfide in natural gas and other petroleum feedstocks to form elemental sulfur polymers (polysulfides) as a means to remove hydrogen sulfide from the fuel products. However, it is previously unknown if oxidized graphene, or another carbon nanomaterial, is capable of catalytically or non-catalytically enhance the oxidization of hydrogen sulfide to form polysulfides in living cells.

Such action could be beneficial under conditions of acute injury such as oxidative stress, and chronic conditions such as diabetes. That action can provide a means to utilize the beneficial effects of hydrogen sulfide as a therapeutic, however, as a substrate rather than the primary therapeutic.

Deficiency of $H_2S$ has been noted in several diseases. This deficiency and the consequent loss of sufficient polysulfides likely contributes to pathology through both loss of sufficient antioxidant capacity and less persulfidation of proteins and thus impairing the function of these proteins.

Alternative materials capable of enhancing the oxidation of hydrogen sulfide safely in vivo are needed in the medical arts in order to provide safe and effective means of generating reductants (antioxidants) in vivo for the annihilation of free radicals and other potentially beneficial effects of polysulfides including persulfidation necessary for proper function of proteins. Such materials can have a variety of applications, particularly in the treatment of diabetes, inflammation associated diseases such as Alzheimer's disease, arthritis, traumatic brain injury (TBI), tissue damage resulting from ischemic or hemorrhagic events and the like.

The present invention, discussed in detail hereinafter, provides non-toxic materials, compositions and therapeutic methods using those materials that catalytically and non-catalytically form polysulfides from hydrogen sulfide in vitro and in vivo to thereby provide one means of addressing the need for safe and effective elimination of harmful free radicals and conversion of $H_2S$ to polysulfides to restore protein persulfidation.

BRIEF SUMMARY OF THE INVENTION

The present invention contemplates a therapeutic method for enhancing the production of persulfide and/or polysulfide from hydrogen sulfide in vitro and in vivo using endogenously or exogenously released hydrogen sulfide. That method comprises contacting cells in need with an effective amount of oxidized carbon nanoparticulate material in which the particles contain a plurality of carbonyl, hydroxyl and carboxyl substituents. Illustrative cells in need include those under oxidative stress, such as in traumatic brain injury (TBI), hypoxia, ischemia, reperfusion injury, and cells in need of sufficient protein persulfidation to ensure proper function of that protein as is needed in a large number of disease processes associated with reduced $H_2S$ and/or polysulfides and/or persulfides.

Contemplated oxidized carbon nanoparticulate material can be prepared from any of a variety of sources including graphene, graphene nanoribbons, graphene oxide, graphite, graphite oxide nanoribbons, carbon black, hydrophilic carbon clusters, oxidized coal, and activated charcoal, which is preferred, and forms oxidized activated charcoal/coal particles (OACs). These materials exhibit strong catalytic redox activity, and formulations of these materials have demonstrated efficacy in animal models of injury.

A means to enhance the generation of polysulfides from $H_2S$ endogenously or exogenously released can increase the effectiveness in conditions in which this agent is pathologically involved. Compared to some preparations of oxidized activated carbon nanomaterials, OACs made from good manufacturing practice (GMP)-prepared activated charcoal contain little to no metal contamination that requires removal.

In one aspect, the oxidized carbon nanoparticulate material can be used as part of a method for catalyzing the oxidation of hydrogen sulfide into persulfides and/or polysulfides within a cell culture and/or living tissue environment. In one embodiment, oxidized carbon nanoparticulate material is functionalized with one or more exogenously-supplied specific substituents that are selected from the group of a hydrogen sulfide-releasing moiety, a solubilizing agent, a biological barrier transporter moiety, a tissue-targeting agent, an assay-identifying agent, a chelating agent and a pharmaceutical agent. The exogenously-supplied specific substituent can be non-covalently bound, or covalently linked to the oxidized carbon nanoparticulate material.

In another aspect of this embodiment, oxidized carbon nanoparticulate material is functionalized with a solubilizing agent selected from one or more of the group consisting of poly(ethylene glycol) [PEG], poly(propylene glycol) [PPG], poly(ethyleneimine) [PEI], poly(vinyl alcohol) [PVA], PPG-PEG block co-polymers, $C_{12}$-$C_{18}$-poly(ethyleneoxide)-ether and poly(acrylic acid) [PAA].

In another aspect of this embodiment, the oxidized carbon nanoparticulate material is conjugated with a hydrogen sulfide-releasing moiety and the hydrogen sulfide released is oxidized in situ by the carbon nanoparticle to generate antioxidant products. Hydrogen sulfide-releasing moieties are preferably covalently linked to the carbon core of the nanomaterial and can provide hydrogen sulfide by thiolysis, or enzymolysis. Illustratively, such materials include N-benzoylthiol-benzamides, acyl perthiols, aryl thioamides, polysulfides, dithioperoxyanhydrides, S-aroylthiox-amines, geminal-dithiols, and trimethyl lock prodrugs.

In another aspect, oxidized carbon nanomaterials are provided as part of a method for increasing polysulfide and/or persulfide concentrations in vivo by catalytic oxidation of endogenous hydrogen sulfide. The resultant increase in polysulfide and persulfide concentrations manifest as a rich therapeutic antioxidant pool and restoration protein persulfidation.

In another aspect, the rate of polysulfide formation can be enhanced or inhibited by additional chemical reactions that can be desirable depending on the indications. As an example, covalent reaction with etheylenediamine enhances the rate of polysulfide formation.

In yet a further aspect, oxidized carbon nanoparticulate material is functionalized with a transporter moiety that is selected from one or more of the group consisting of adamantanyl, amantadinyl, memantinyl, rimantadinyl, dopamantinyl, tromantadinyl, vildagliptinyl and karmantadinyl groups.

In another aspect, oxidized carbon nanoparticles are functionalized with a chelating agent such as, but not limited to deferoxamine and deferasirox intended to bind toxic materials such as iron in conditions in which that metal is in excessive concentrations either systemically, such as iron overload, or locally, such as in a hemorrhage or as part of pathological processes such as dementia.

In a particular aspect, the method provides for using the persulfides and polysulfides in therapeutic applications, such as in the treatment of conditions associated with inflammation, ischemia or neurodegeneration in a subject.

In some embodiments, a composition comprising oxidized carbon nanomaterials in a therapeutic preparation suitable for use in a subject is provided. Here, oxidized carbon nanoparticulate material can be functionalized with a pharmaceutical agent that is a cannabinoid. Illustrative cannabinoids include cannabigerol, cannabigerol monomethyl ether, cannabinerolic acid A, cannabigerovarin, cannabigerolic acid A, cannabigerolic acid A monomethyl ether, cannabigerovarinic acid A, cannabichromene, cannabichromenic acid A, cannabivarichromene, cannabichromevarin, cannabichromevarinic acid A, cannabidiol, cannabidiorcol, cannabidiolic acid, cannabidivarinic acid, cannabinodiol, cannabinodivarin, cannabivarin, cannabicitran, 1,1-dimethyl-heptyl-11-hydroxytetrahydrocannabino) (HU-210), and dexanabinol.

In particular embodiments, the compositions of modified carbon nanomaterials, particularly oxidized carbon nanomaterials (nanoparticles), comprise carboxy-functionalized carbon-based nanoparticles. These materials are provided as a therapeutic preparation suitable for enhancing the production of polysulfides by a cell. By way of example, the carbon nanomaterials in the therapeutic preparation comprise: graphene, graphene nanoribbons, graphene oxide, graphite, graphite oxide nanoribbons, carbon black, oxidized carbon black, hydrophilic carbon clusters (HCCs), oxidized activated coal, oxidized activated charcoal or any combination thereof.

One preferred group of oxidized carbon nanoparticles (CNPs) is prepared using nitric acid-oxidized or fuming nitric acid-oxidized activated charcoal particles that are subsequently functionalized with polyethylene glycol (PEG-OAC). The activated charcoal used is preferably made from medicinal grade and/or good manufacturing practice (GMP)-prepared activated charcoal. The oxidation process can also be run using nitric acid or fuming nitric acid mixed with sulfuric acid or fuming sulfuric acid as the oxidizing medium.

The oxidation reactions discussed herein have been carried out in a static nitric acid bath that is potentially dangerous because the reactants can be explosive. The reaction process can also be carried out in a flow device that is less dangerous. The concentration and temperature can be varied to yield suitable particle characteristics.

Various quenching methods can be utilized. Water addition has been used, as have aqueous solutions of organic and inorganic bases, but a glycine quench is preferred because it acts as a buffer and rapidly removes the nitric acid.

By way of example, some of the carbon nanoparticles comprise a hydrophilic carbon cluster (HCC) or a polyethylene glycol-conjugated hydrophilic carbon cluster (PEG-HCC). The compositions are described as having a rapid and high capacity antioxidant activity, and as being non-toxic in vitro and in vivo.

Previously reported oxidized carbon nanoparticles known to the inventors form dispersions in water that exhibit separation of the particles from the dispersion within about an hour, and remain on top of a 0.22 μm diameter pore size polyethersulfone (PES) filter membrane rather than passing through the filter, exhibit an UV maximum of about 250 nm, and contain about contain about 4 to about 7 percent carbonyl groups by X-ray photoelectron spectroscopy (XPS). PEG-OAC materials have been shown to have similar antioxidant effects and in vivo protection as PEG-HCC.

A new type of oxidized carbon nanoparticulate material is also contemplated. These particles are discoid in shape and form a non-separating dispersion in water at a concentration of about 1 to about 5 mg/mL. The dispersion is stable to separation at ambient room temperature for at least seven days. The oxidized carbon nanoparticulate dispersion in water exhibits an UV absorbance maximum at about 220 nm. The particles contain about 9 to about 15 percent carbonyl groups by X-ray photoelectron spectroscopy (XPS), and pass through a 0.22 μm pore size polyethersulfone (PES) filter membrane.

The oxidized carbon nanoparticulate material can itself be added directly to a cell culture or used as a powder in a spray. Preferably, contemplated oxidized carbon nanoparticulate materials are utilized dissolved or dispersed in a physiologically tolerable diluent or carrier such as a solid or liquid pharmaceutical composition.

As so formulated, a contemplated composition can be provided to a subject as a pill or tablet, as a liquid to be swallowed or infused percutaneously as by intravenous, intra-muscular, subcutaneous, intradermal or intraperitoneal injection, or as a topical treatment to the skin and/or mucosa, or as an intranasal spray or mist or as an inhalant.

BRIEF DESCRIPTION OF THE DRAWINGS

In the drawings forming a portion of this disclosure,

FIG. 10B further shows how concentration (0.1, 1, 4, 10 mg/L) of PEG-HCCs and EN-PEG-HCCs affect SSP4 fluorescence in a cell-free solution with sodium sulfide. EN-PEG-HCCs react more rapidly at equivalent concentrations.

PEG-HCC (circles), PEG-OAC (squares). The reduction with PEG-OAC is faster than with PEG-HCC.

Figure 13:
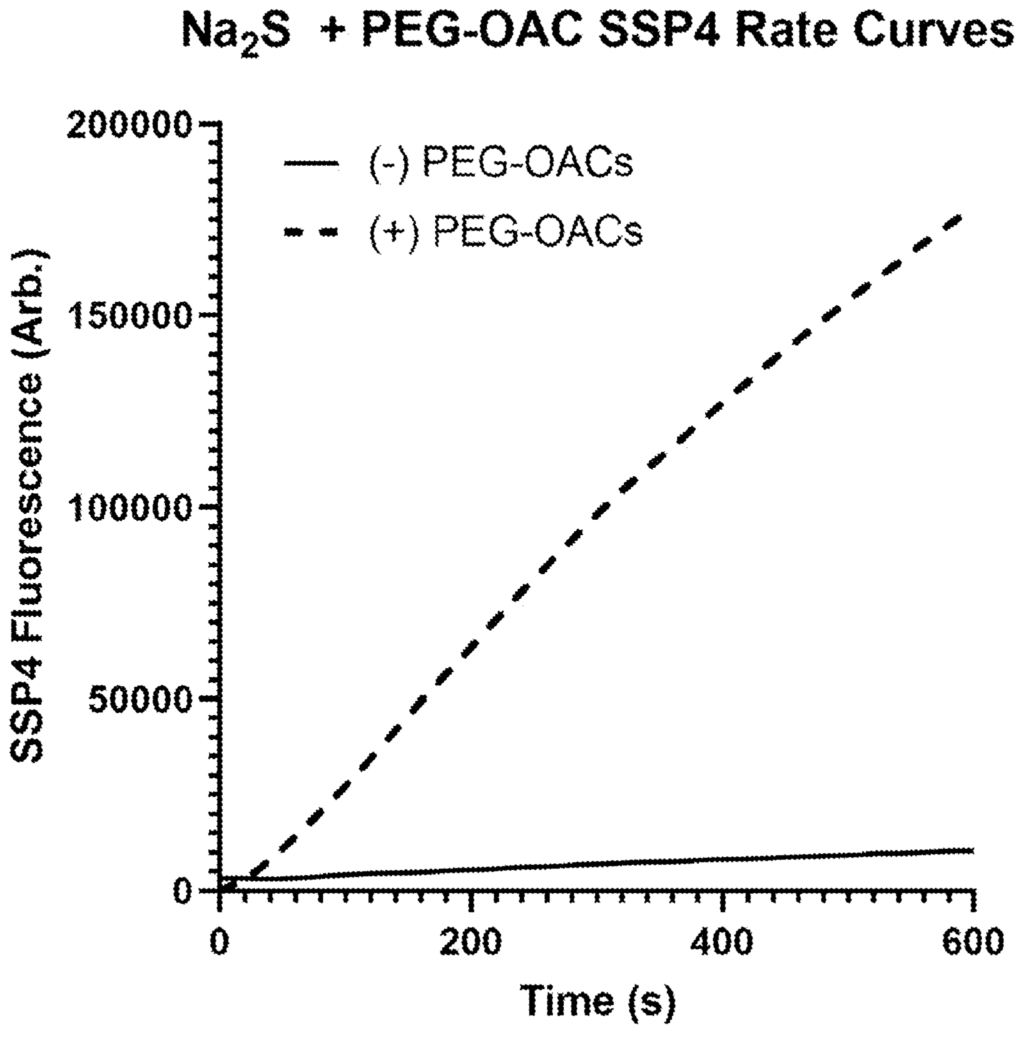

FIG. 13 is a graph showing the rate of polysulfide formation in the presence (dashed line) and absence (solid line) of 4 mg/L PEG-OACs added to a cell-free aqueous PBS solution containing 300 μM $Na_2S$ and 10 μM fluorescent sulfur probe (SSP4). Fluorescence was measured at 540 nm for 10 minutes, in which time the polysulfide formation rate was increased by a factor of 30-fold due to the presence of PEG-OAC as indicated by the fluorescence.

Figure 14:
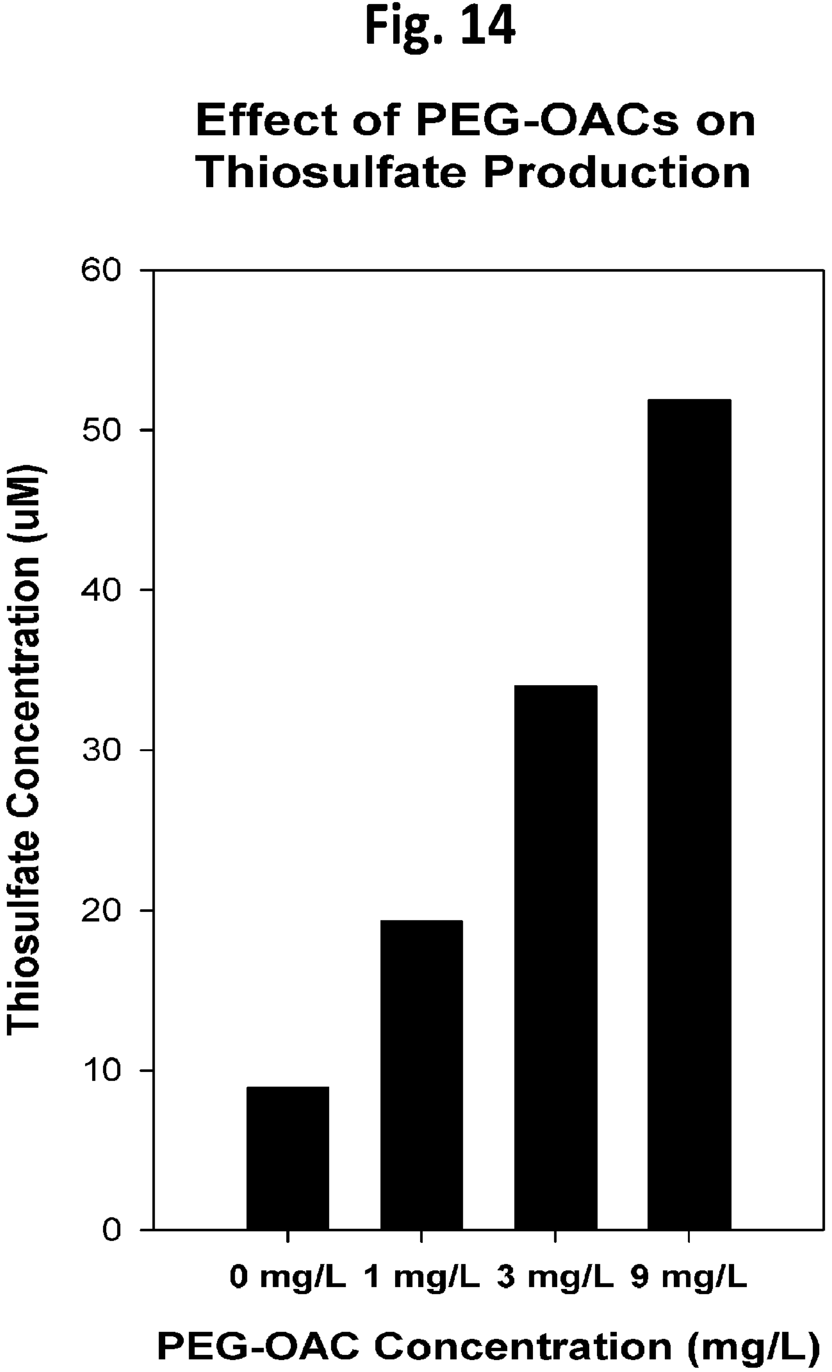

FIG. 14 is a graph showing PEG-OAC dose-dependent (zero, 1, 3 and 9 mg/L) production of thiosulfate in which the PEG-OACs were added to a cell-free aqueous PBS solution containing 300 μM $Na_2S$. Thiosulfate production was determined by the method of Dong et al., *ACS Sens.* 2017; 2(8):1152-1159. Thiosulfate is a product of polysulfide oxidation and indictive of polysulfide production.

Figure 15:
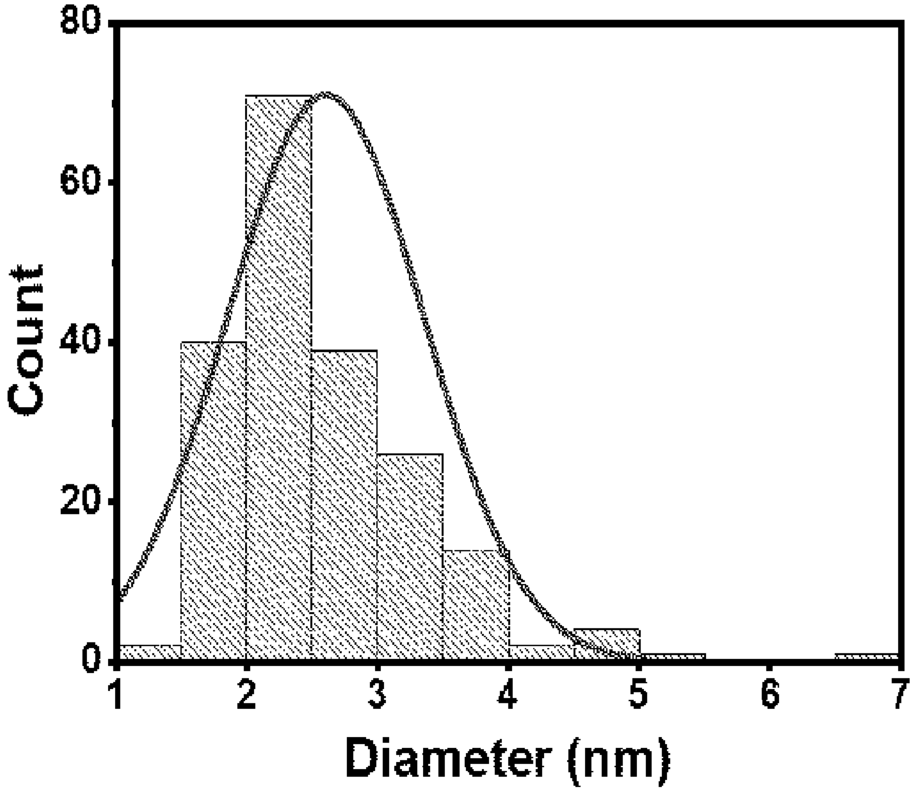

FIG. 15 is a graph that illustrates particle distribution when OAC particles were prepared using fuming nitric acid (90% $HNO_3$) at 100° C. for 6 hours. The particles of the mixture have a mean diameter of 2.8 nm.

Figure 16:
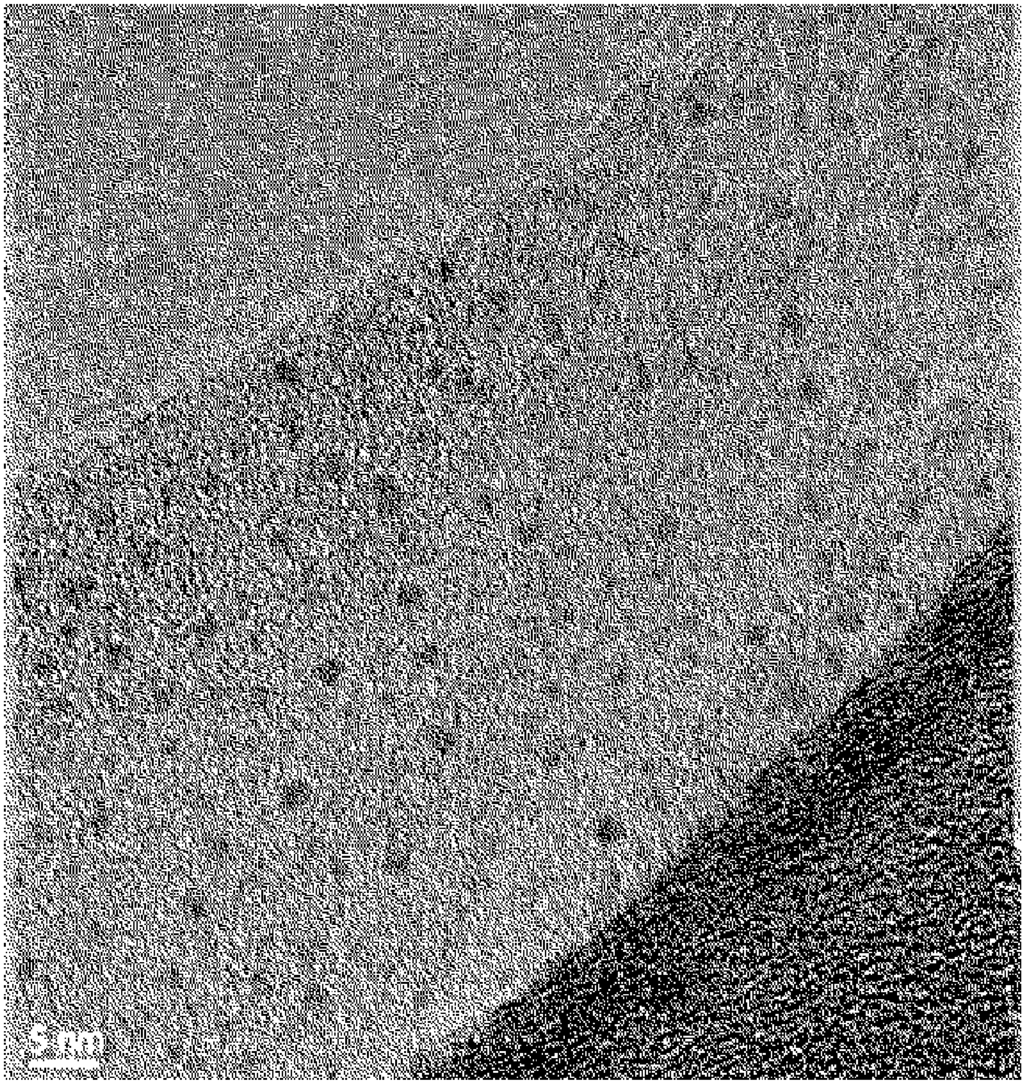

FIG. 16 is a transmission electron microscope image of OAC nanoparticles on lacey carbon. The nanoparticles appear as dark circles and have an average diameter of 2.8 nm.

Figure 17:
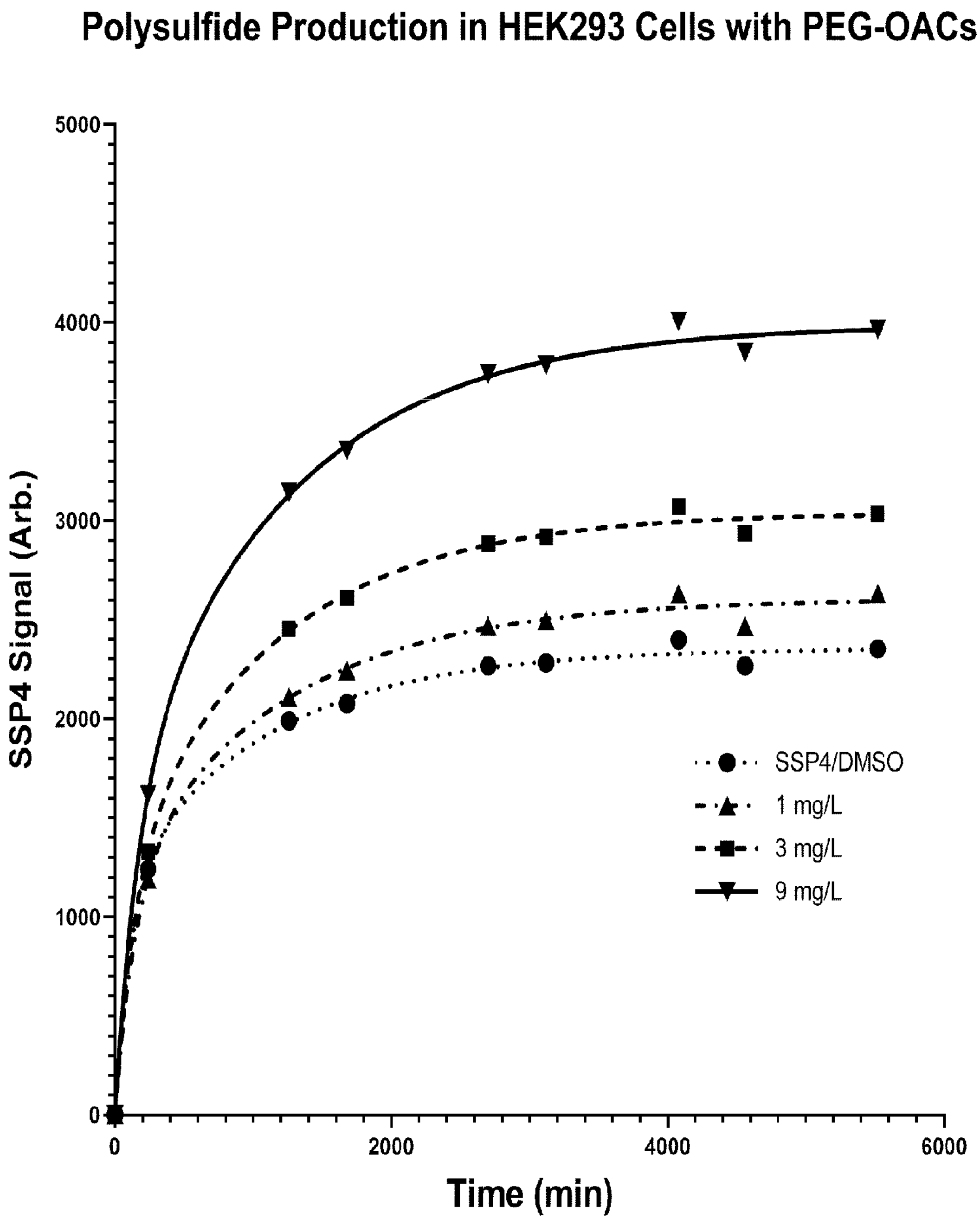

FIG. 17 is a graph that illustrates that PEG-OACs increase the rate of polysulfide production in HEK293 cells without additional sulfide donor. Polysulfide production in HEK293 cells was measured by ssp4 (y axis, arbitrary units) is catalyzed by PEG-OACs in a dose-dependent manner (0, 1, 3, 9 mg/L).

Figure 18:
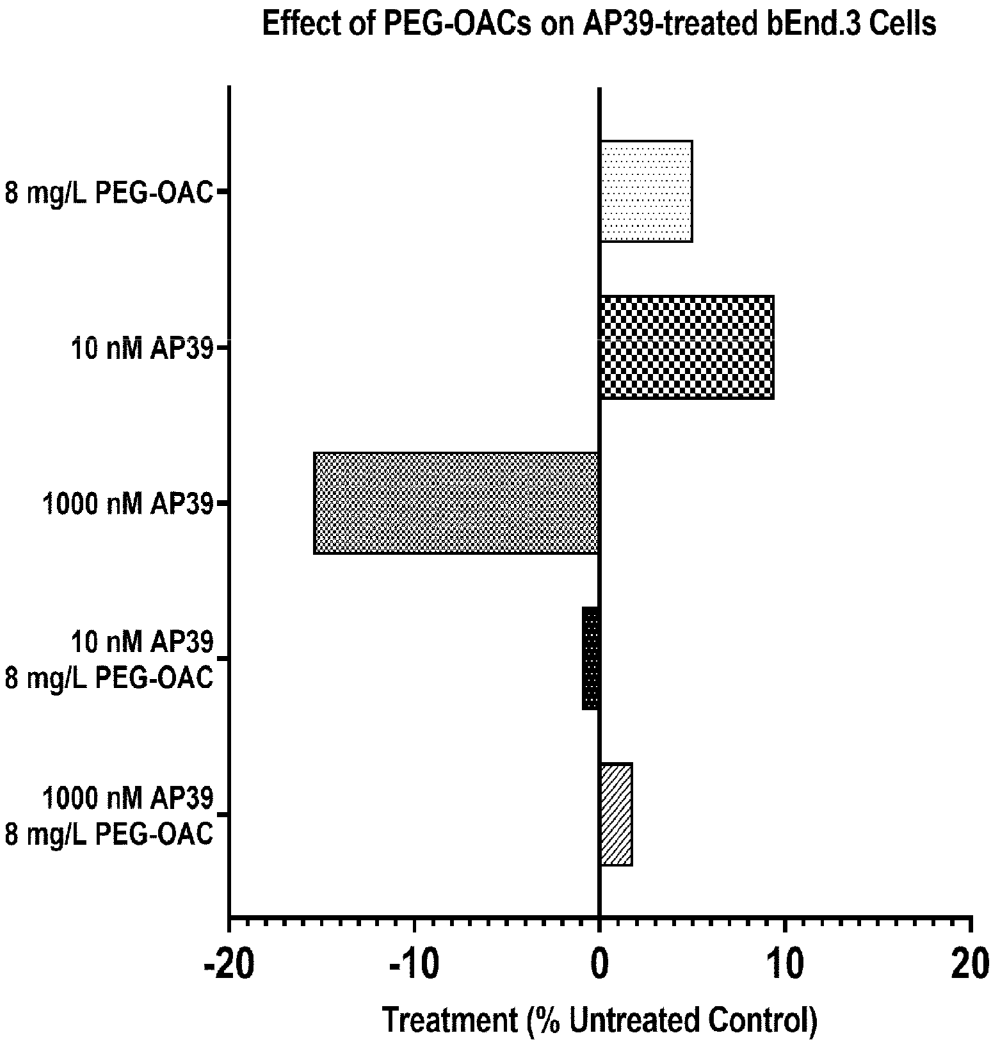

FIG. 18 PEG-OACs reduce both the proliferative and toxic effects of the mitochondrial $H_2S$ donor 10-oxo-10-(4-(3-thioxo-3H-1,2-dithiol-5yl)phenoxy)decyl)triphenylphosphonium bromide (AP39) [Szczesny et al., *Nitric Oxide* 2014; 14:120-130]. As is seen, PEG-OACs reduce 10 nM AP39-induced proliferation in bEnd.3 cells and reduce 1000 nM AP39-induced toxicity in those cells.

Figure 19:
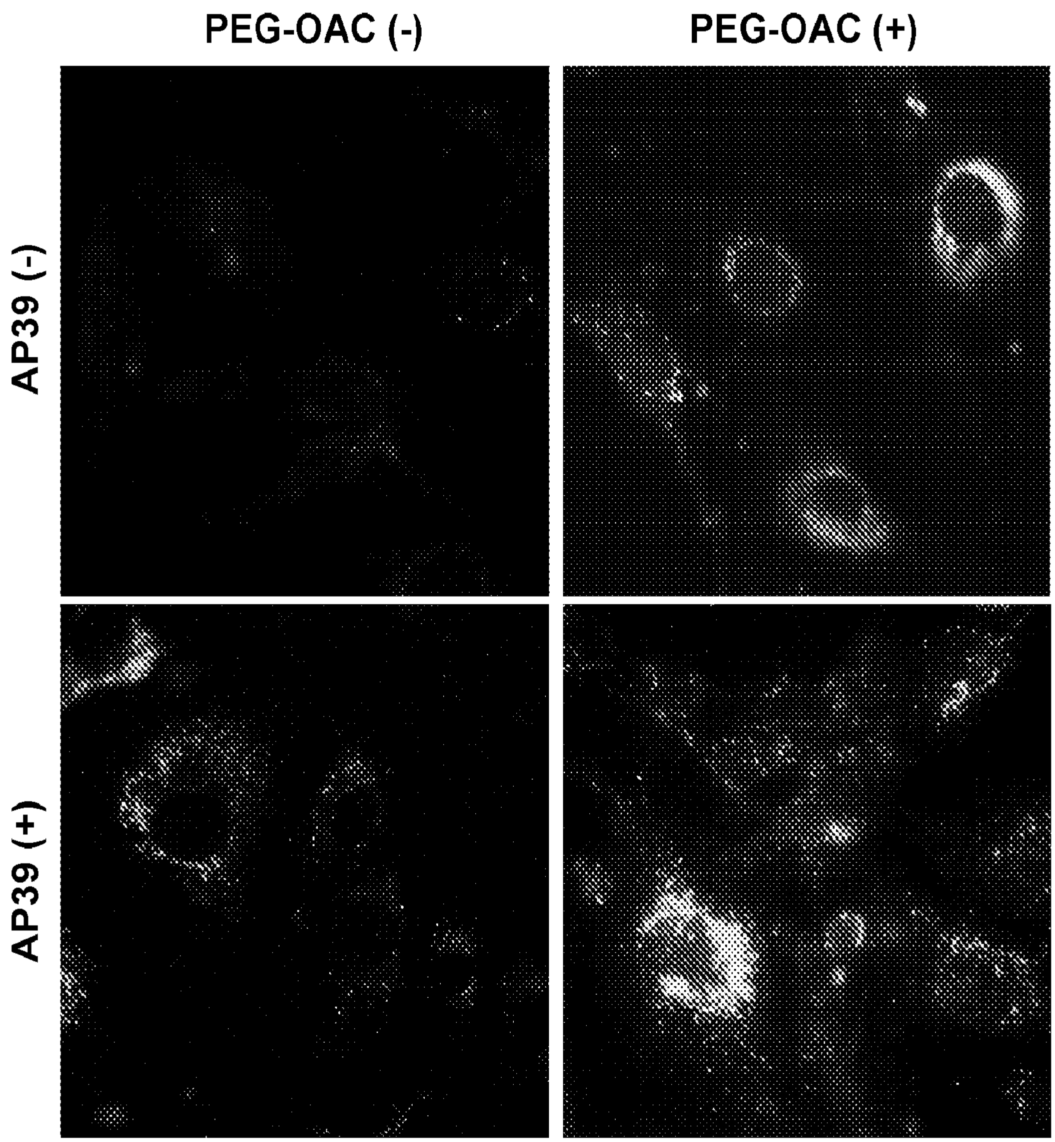

FIG. 19 shows fluorescence photomicrographs of bEnd.3 cells with no additive [AP39(−)/PEG-OAC(−)], treated with AP39 alone [AP39(+)/PEG-OAC(−)], PEG-OACs alone [AP39(−)/PEG-OAC(+)] or with both [AP39(+)/PEG-OAC (+)]. The presence of 4 mg/L PEG-OACs with bEnd.3 cells causes an increase in the fluorescence of polysulfide-sensitive sulfur sensing probe 4 (SSP4) relative to the control [AP39(−)/PEG-OAC(+)] in the absence of AP39. Addition of AP39 also increases the fluorescence signal, however addition of PEG-OACs amplifies this effect [AP39(+)/PEG-OAC(+)].

Definitions

The following definitions are employed in the following description:

It is understood that aspect and embodiments of the invention described herein include "consisting" and/or "consisting essentially of" aspects and embodiments.

The articles "a" and "an" are used herein to refer to one or to more than one (i.e., to at least one) of the grammatical object of the article. By way of example, "an element" means one element or more than one element.

Reference to "about" a value or parameter herein includes (and describes) variations that are directed to that value or parameter per se. For example, description referring to "about X" includes description of "X".

As used herein, the term "anti-cancer agent" refers to a pharmacologically active agent that is capable of inhibiting a cancer selected from the group consisting of melanoma, glioma, and adenocarcinoma, bladder cancer, bone cancer, cancer of the bone marrow, brain cancer, spinal cancer, breast cancer, cervical cancer, gall bladder cancer, cancer of the ganglia, cancer of the gastrointestinal tract, stomach cancer, colon cancer, cancer of the heart, kidney cancer, liver cancer, lung cancer, muscle cancer, ovarian cancer, pancreatic cancer, parathyroid cancer, cancer of the penis, prostate cancer, cancer of the salivary glands, skin cancer, cancer of the spleen, cancer of the testis, thymus cancer, thyroid cancer, or uterine cancer.

DETAILED DESCRIPTION OF PREFERRED EMBODIMENTS

The present invention contemplates a therapeutic method for catalytically forming persulfide and/or polysulfide from hydrogen sulfide in vitro and in vivo using endogenously or exogenously released hydrogen sulfide. That method comprises contacting cells in need with an effective amount of oxidized carbon nanoparticulate material in which the particles contain a plurality of carbonyl, hydroxyl and carboxyl substituents.

Exemplary cells in need are those present in a mammalian subject whose body is under oxidative stress, from, and not limited to, traumatic brain injury (TBI), inflammation, sepsis, and hypoxia as can occur from epileptic seizure, stroke or thrombosis, shock, organs prepared for transplantation or implantation. Exemplary cells are in need in a mammalian subject whose body has insufficient $H_2S$ to generate sufficient persulfidated proteins or insufficient innate capacity to generate sufficient persulfidated proteins for proper function in, but not limited to, aging, cancer, inflammation, diabetes, stroke, trauma and reduce potential toxicity from excess $H_2S$.

Contemplated oxidized carbon nanoparticulate material can be prepared from any of a variety of sources including graphene, graphene nanoribbons, graphene oxide, graphite, graphite oxide nanoribbons, carbon black, hydrophilic carbon clusters (HCCs), oxidized coal, activated coal, and activated charcoal, which is preferred and forms oxidized activated charcoal particles (OACs).

Figure 1:
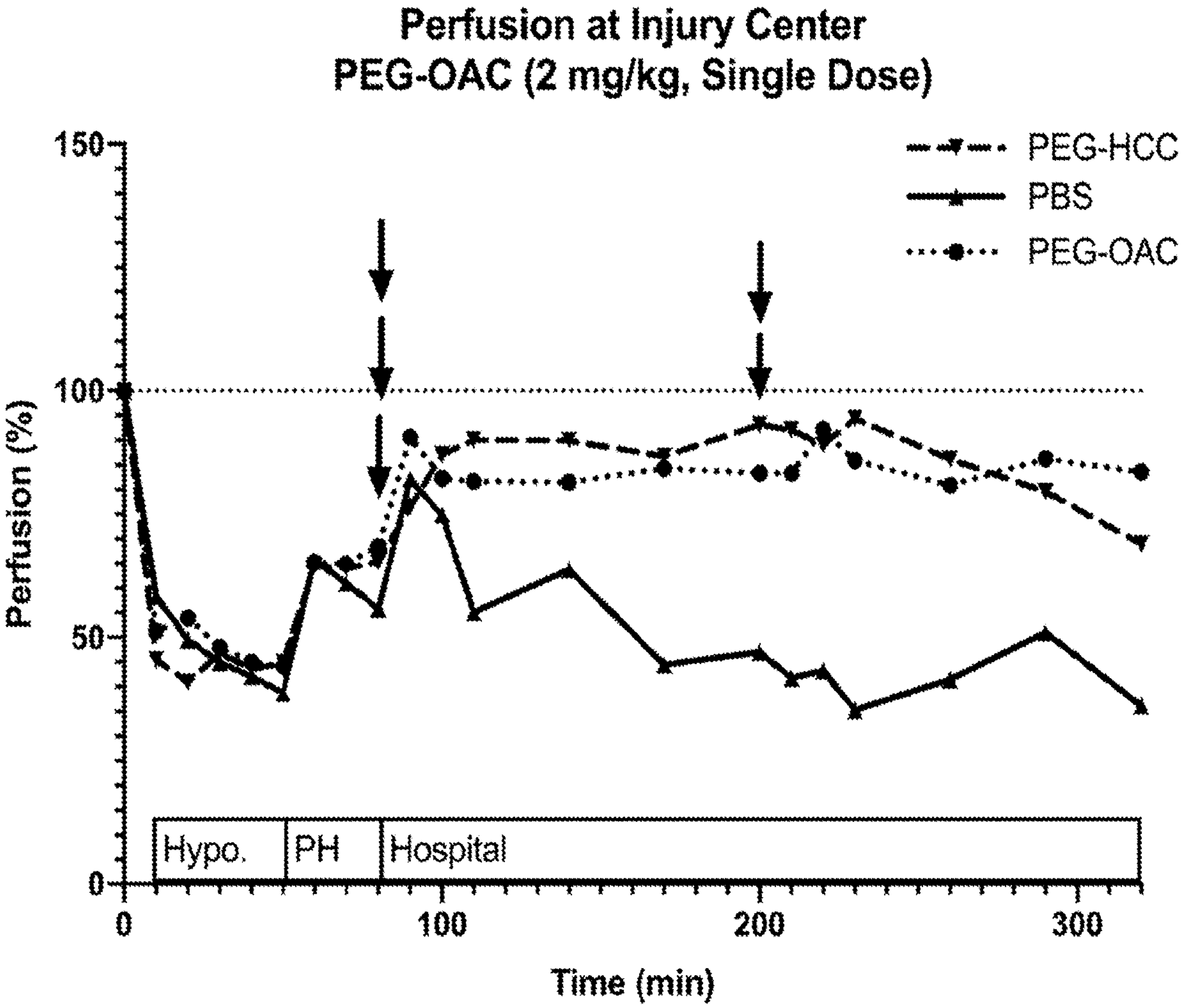
FIG. 1 is a graph showing perfusion over time in the presence of PBS (solid line), PEG-OAC (dotted line) and PEG-HCC (dashed line) in the restoration of cerebral blood flow in a rat model of traumatic brain injury in which it is seen that results with PEG-OAC are comparable to those seen with PEG-HCCs. Traumatic brain injury occurs at Time 0, followed by reduction of blood pressure by withdrawal of blood, which because of the brain injury, lowers cerebral perfusion (y axis). At PH (pre-hospital phase), saline is infused which transiently increases brain perfusion. At "Hospital phase", the rat is resuscitated with the stored blood along with injection of either PBS (vehicle), PEG-HCC or PEG-OAC. Perfusion in the PBS group transiently increases but then continues to decline, while both nanoparticles (NPs) sustain an increase in perfusion throughout the experiment, with a second injection in the PEG-HCC group but was not required in the PEG-OAC group.

OACs exhibit strong catalytic redox activity, and formulations of these materials have demonstrated efficacy in an in vivo rodent traumatic brain injury model shown in FIG. 1. Compared to some preparations of oxidized activated carbon nanomaterials, OACs made from good manufacturing practice (GMP)-prepared activated charcoal contain little to no metal contamination that requires removal.

A means to enhance the generation of polysulfides from $H_2S$ endogenously or exogenously released can increase the effectiveness in conditions in which this agent is pathologically involved.

In one embodiment, the oxidized carbon nanoparticulate material can be used as part of a method for catalyzing the oxidation of hydrogen sulfide into persulfides and/or polysulfides within a cell culture and/or living tissue environment. In one aspect, oxidized carbon nanoparticulate material is functionalized with one or more exogenously-supplied specific substituents that are selected from the group of a hydrogen sulfide-releasing moiety, a solubilizing agent, a biological barrier transporter moiety, a tissue-targeting agent, an assay-identifying agent, a chelating agent and a pharmaceutical agent. The exogenously-supplied specific substituent can be non-covalently bound, or covalently linked to the oxidized carbon nanoparticulate material.

In some aspects, an active agent can be associated with the carbon nanomaterial, covalently or non-covalently. For example, the carbon nanomaterials can be functionalized with one or more molecules, chelating agents such as deferoxamine, polymers, chemical moieties, and the nanoparticles can contain functional or solubilizing groups such as ketones, alcohols, epoxides, carboxylic acids, 1,2-diones, 1,4-diones, 1,2-quinones, 1,4-quinones and combinations thereof.

More specifically, the oxidized carbon nanomaterials can be functionalized with any number of solubilizing polymers. Exemplary solubilizing polymers include one or more of poly(ethylene glycol) [PEG], poly(propylene glycol) [PPG], poly-(ethyleneimine) [PEI], poly(vinyl alcohol) [PVA] and poly(acrylic acid) [PAA] or any combination of these polymers. As is well known, these solubilizing polymers are available in many lengths (molecular weights), with a number being utilized herein and exemplified in the FIGS. Solubilizing polymers or functionalizing groups can be covalently or non-covalently associated with the oxidized carbon nanomaterials, for example, as oxidized carbon nanomaterials can be non-covalently wrapped with a plurality of solubilizing groups such as PEG, PPG or block co-polymers of PEG and PPG such as a Pluronic® polyol (PEG-PPG-PEG). In some embodiments, the solubilizing group is covalently bound to the particle.

The oxidized carbon nanomaterials (nanoparticles) as part of a therapeutic composition can also include a targeting agent that can be covalently attached or non-covalently bonded to the nanoparticulate. By way of example, such targeting agents can comprise an antibody, RNA, DNA, an aptamer, a small molecule, a dendrimers, a protein or peptide, saccharide, polysaccharide or any combination of these.

A targeting agent exhibits a recognition activity for a marker related to the need of the contacted cell to be fulfilled such as relieving oxidative stress. For example, an exemplary marker can be a cell surface protein that is up-regulated in response to oxidative stress, or a carbohydrate recognition element. The particular targeting agent is selected based on the affinity and/or specificity of the particular target agent for a specific cell type or a particular sub-cellular organelle within or at a target site of a cell in need.

A therapeutic composition of the present invention can also be associated with a chelating agent so as to enhance its ability to remove excess metal or other agents as part of a pathological process in which reduction in the levels of that agent is beneficial. By way of example, the chelating agent could be deferoxamine, diethylenetriaminepentaacetic acid (pentetic acid or DTPA), deferasirox, deferiprone, aerobactin, triapine, salicylaldehyde isonicotinoyl hydrazone, (E)-N9-[1-(2-hydroxy-5-nitrophenyl)-ethyliden]isonicotinoyl hydrazone, di-pyridyl ketone isonicotinoyl hydrazone, D-penicillamine, or structural derivatives thereof to enable conjugation to the nanoparticle.

A therapeutic composition of the present invention can also be associated with a transporter moiety, so as to better facilitate the transport of the oxidized carbon nanomaterials through a biological barrier; i.e., the blood brain barrier (BBB) and blood spinal cord barrier (BSCB). By way of example, these transporter moieties can comprise an adamantine molecule, or an adamantane derivative. Illustrative adamantine derivatives can include amantadine, memantine, rimantadine, dopamantin, tromantadine, vildagliptin, karmantadin, and any combination thereof. As substituents, these compounds are referred to as adamantanyl, amantadinyl, memantinyl, rimantadinyl, dopamantinyl, tromantadinyl, vildagliptinyl and karmantadinyl groups.

The transporter moieties that can be used with the oxidized carbon nanomaterials can comprise a cannabinoid molecule or a cannabinoid derivative, including, for example and not limitation, cannabigerol, cannabigerol monomethyl ether, cannabinerolic acid A, cannabigerovarin, cannabigerolic acid A, cannabigerolic acid A monomethyl ether, cannabigerovarinic acid A, cannabichromene, cannabichromenic acid A, cannabivarichromene, cannabichromevarin, cannabichromevarinic acid A, cannabidiol, cannabidiorcol, cannabidiolic acid, cannabidivarinic acid, cannabinodiol, cannabinodivarin, cannabivarin, cannabicitran, HU-210 (1,1-dimethyl-heptyl-11-hydroxytetrahydrocannabinol), or dexanabinol (HU-211).

The transporter moiety can be associated with the carbon nanomaterials in various manners, such as by being covalently linked to the edges or faces of the carbon nanomaterials. The covalent linkage can occur directly between moiety and particle or through a linker molecule, can be associated with the end of a solubilizing chain, or one or more transporter moieties can be non-covalently linked to the oxidized carbon nanomaterials.

In some embodiments, the therapeutic composition can comprise anti-inflammatory drugs, anti-cancer drugs, anti-diabetic drugs, and combinations of these agents.

The carbon nanomaterials disclosed herein can be used as MRI tracers to enable real-time tracking, distribution and delivery of an administered therapeutic composition to a subject. In this case other elements such as gadolinium can be beneficial for enhanced contrast, and these are often affixed via a conjugated chelator.

Methods of Treatment and Pharmaceutical Compositions

A method of forming persulfide and/or polysulfide from hydrogen sulfide is contemplated. That method comprises contacting cells in need with an effective amount of oxidized carbon nanoparticulate material in which the particles contain a plurality of carbonyl, hydroxyl and carboxyl substituents.

As part of a method for treating a subject and its cells in need of treatment, a contemplated method provides for a reduction of free-radical species, and hence, provides for a reduction in free radical pathology that is typically attendant to an injury site in or on a subject. By way of example, a treatment method can be described as providing a reduction in the level of reactive oxygen species at a target site of a subject by about 5% to about 50%.

Another contemplated method provides for increase in persulfidation of proteins to restore function in which persulfidation of proteins is required for their proper actions.

The oxidized carbon nanomaterials also provide for minimal toxicity to the subject being treated.

In some embodiments, oxidized carbon nanomaterials can be described as hydrophilic, hydrophobic, or amphiphilic (amphiphilic, permitting aqueous solubility with noncovalent binding of hydrophobic molecules such as drugs or diagnostic labels) and, by way of example and not limitation, can resemble micelles or liposomes. Additionally, the carbon nanomaterials can entrap further active agents for delivery to a site—thus active agent efficacy and antioxidant properties.

In yet other embodiments, an oxidized carbon nanomaterial can be modified to include a hydrogen sulfide donor moiety. $H_2S$ donor skeletons based on compounds with known biological activity are shown below, classified by their mechanism of $H_2S$ release, as discussed in Powell et al., *Biochem Pharmacol* 149:110-123 (2018). These materials are discussed in Example 4 hereinafter.

Thiol-triggered $H_2S$ donors react with thiols and have a diverse array of reactive moieties with N-benzoylthiolbenzamides, acyl perthiols, polysulfides, dithioperoxyanhydrides, and S-aroylthioxamines filling this category. Two enzyme-triggered structural motifs also exist, germinal-dithiols, and trimethyl locked prodrugs. All of these skeletons can be modified with unique R and R' groups that can facilitate conjugation to linker molecules or nanoparticles directly, as are well known in the art.

In some embodiments, an oxidized carbon nanomaterial can include an active agent, wherein the active agent is associated with the oxidized carbon nanomaterial, covalently or non-covalently. For example, an active agent can comprise an anti-cancer drug, a chemotherapeutic agent, an antioxidant, an anti-inflammatory drug, or any combination of these active agents can be a small molecule, protein, aptamer, DNA, anti-sense oligo nucleotide, miRNA, siRNA, and combinations thereof.

By way of example, any one or more of the active agents can be covalently associated with an oxidized carbon nanomaterial through a cleavable moiety (i.e. ester bond/amide bond), photo-cleavable moiety, or pH-sensitive cleavable moiety. Additional modes associated with carbon nanomaterials can also be envisioned.

In yet another embodiment, a method for treating oxidative stress is provided, wherein reactive oxygen species levels in a subject are reduced by administering a preparation of oxidized carbon nanoparticles to the subject. In particular applications, the preparation can be provided as a localized treatment preparation at a site in and/or on a subject (FIG. 1). Methods for reducing reactive oxygen species (ROS), reactive sulfur species (RSS) or other radical stressors and those yet to be characterized, levels to homeostatic levels or pre-suffered stress levels are also provided comprising administering a preparation of the oxidized carbon nanoparticles.

The treatment preparations and methods can be functioning to reduce ROS and RSS by any number of mechanisms, including by attenuating the generation of reactive species, and/or by mitigating reactive species-induced consumption of endogenous anti-oxidant enzymes. As part of a therapeutic treatment, it is contemplated that a reduction of ROS provided by the administration of the preparation can be accomplished by, for example, determining the changes in intensity of a dye or marker that is specific for one or more reactive oxygen species.

In yet another embodiment, a method of restoration of persulfidation of proteins is provided. The treatment preparations and methods of their use are thought to function by enhancing generation of persulfides and/or polysulfides from $H_2S$ by administration of the oxidized carbon nanoparticles to the subject. Insufficient persulfidation contributes to a range of diseases in which enhancing generation of persulfides and/or polysulfides would be desirable. The extent of protein persulfidation can be measured such as by mass spectrometry as indication of treatment effect.

The usage of the material, with the hydrogen sulfide within a cell to metabolize the hydrogen sulfide into therapeutic products—is combined with the hydrogen sulfide donors to insert the beneficial polysulfide into a target site of a subject.

A contemplated oxidized carbon nanoparticulate material can be used in the manufacture of a medicament (pharmaceutical composition) that is useful at least for forming persulfide and/or polysulfide from hydrogen sulfide. A contemplated oxidized carbon nanoparticulate material, medicament or pharmaceutical composition containing the same forms persulfide and/or polysulfide by contacting cells in vitro, or in vivo as in a subject in need thereof. When so used, pharmaceutically acceptable salts, buffers and the like are typically present that collectively are referred to as pharmaceutically acceptable diluents as compared to those that can be present in a composition that is not intended for pharmaceutical use.

A contemplated oxidized carbon nanoparticulate material is frequently present as a carboxylic acid and/or carboxylate anion. A cation such as monovalent lithium, sodium, potassium, and ammonium ions, or a divalent ion such as magnesium or calcium can be present to balance the charge of a carboxylate group.

Inasmuch as amine-containing compounds can also be associated with the contemplated particles, either linked covalently or non-covalently or merely bound by hydrophobic or hydrophilic or other forces. Where a solubilizing agent such as PEI is associated with the particles, it is likely that the number of positive charges from that polymer's protonated amine groups will outnumber the negative charges of the particles' carboxylates at the usually near neutral pH value of most bodily fluids or cell culture media contemplated. Anionic groups can therefore be present to balance the positive charges.

Illustrative useful anions include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

A contemplated pharmaceutical composition contains a persulfide- and/or polysulfide-forming amount of a contemplated oxidized carbon nanoparticulate material or a pharmaceutically acceptable salt thereof dissolved or dispersed in a physiologically (pharmaceutically) acceptable carrier. Such a composition can be administered to mammalian cells in vitro as in a cell culture to contact those cells, or the cells can be contacted in vivo as in a living, host mammal in need.

The data for the FIGS. show that concentrations of about 0.1 to about 10 mg/L, and 2 mg/kg provide effective amounts in the present studies. Skilled workers can readily utilize those amounts to find an effective amount for a particular treated subject or cells to be treated.

A contemplated composition is typically administered in vivo to a subject in need thereof a plurality of times within one month, such as weekly, and can be administered over a period of several months to several years. More usually, a contemplated composition is administered a plurality of times over a course of treatment.

A contemplated pharmaceutical composition can be administered orally (perorally) or parenterally, which is preferred, in a formulation containing conventional nontoxic pharmaceutically acceptable carriers, adjuvants, and vehicles as desired. The term parenteral as used herein includes subcutaneous injections, intravenous (which is most preferred), intramuscular, intrasternal injection, or infusion techniques. Formulation of drugs is discussed in, for example, Hoover, John E., Remington's Pharmaceutical Sciences, Mack Publishing Co., Easton, Pennsylvania; 1975 and Liberman, H. A. and Lachman, L., Eds., *Pharmaceutical Dosage Forms*, Marcel Decker, New York, N.Y., 1980.

Solid dosage forms for oral administration can include capsules, tablets, pills, powders, and granules. The amount of a contemplated compound in a solid dosage form is an effective amount as discussed previously. A solid dosage form can also be administered a plurality of times during a one-week time period.

In such solid dosage forms, a compound of this invention is ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration.

Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution, phosphate-buffered saline. Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Other liquid pharmaceutical compositions include, for example, solutions suitable for parenteral administration. Sterile water solutions of the oxidized-carbon nanoparticles active component or sterile solution of the active component in solvents comprising water, ethanol, or propylene glycol are examples of liquid compositions suitable for parenteral administration. In some aspects, a contemplated oxidized-carbon nanoparticle material is provided as a dry powder that is to be dissolved (dispersed) in an appropriate liquid medium such as sodium chloride for injection prior to use.

In another embodiment, a contemplated composition is designed to be used topically. As such, it is preferred that the viscosity of the composition be greater than that of drinking water. It is preferred that the viscosity be between that exhibited by heavy cream or motor oil and mayonnaise at room temperature. These viscosities are otherwise comparable to those of a hand cream or lotion as compared to an ointment. Thus, one preferred composition can be poured readily at room temperature. Other preferred compositions such as gels tend to pour only with great difficulty if at all at room temperature, and maintain a peaked shape for several seconds after being scooped from a container and formed in to a mound in another.

A contemplated topically-administered pharmaceutical composition need not be applied by hand or spatula, for example, but can be applied via a transdermal patch that adheres to the skin or mucus membrane that is to be treated. In such a patch, the pharmaceutical composition is retained within a composition-permeable reservoir that is usually arrayed upon a flexible planar surface in which the reservoir is surrounded on that flexible surface by adhesive material. The reservoir and adherent flexible surface need not be unitary, but can be separate entities.

The desired ranges in viscosity are typically achieved with the assistance of one or more polymeric thickeners. Illustrative polymeric thickeners include the starch derivatives Zeina B862 hydroxypropyl starch phosphate, and Zeina B860 hydroxypropyl starch. A polysaccharide gum is another useful thickener that can be present in a contemplated composition.

Suitable representative gums are those in the galactomannan gum category. A galactomannan gum is a carbohydrate polymer containing D-galactose and D-mannose units, or other derivatives of such a polymer. There are a relatively large number of galactomannans, which vary in composition depending on their origin. The galactomannan gum is characterized by a linear structure of β-D-mannopyranosyl units linked (1→6). Single membered α-D-manopyranosyl units, linked (1→6) with the main chain, are present as side branches. Galactomannan gums include guar gum, which is the pulverized endosperm of the seed of either of two leguminous plants (*Cyamposis tetragonalobus* and *psoraloids*) and locust bean gum, which is found in the endosperm of the seeds of the carob tree (*Ceratonia siliqua*).

Other suitable representative gums include agar gum, carrageenan gum, ghatti gum, karaya gum, rhamsan gum and xanthan gum. A composition of the present invention can contain a mixture of various gums, or mixture of gums and acidic polymers.

Gums, and galactomannan gums in particular, are well-known materials. See for instance, *Industrial Gums: Polysaccharides & Their Derivatives*, Whistler R. L. and BeMiller J. N. (eds.), 3rd Ed. Academic Press (1992) and Davidson R. L., *Handbook of Water-Soluble Gums & Resins*, McGraw-Hill, Inc., New York (1980). Most gums are commercially available in various forms, commonly a powder, and ready for use in foods and topical compositions. For example, locust bean gum in powdered form is available from Tic Gums Inc. (Belcam, Md.).

A polysaccharide gum, when used, is typically present at about 0.5 percent to about 5 percent, based on the total weight of the composition, with the preferred amount being about 0.5 percent to about 2 percent.

An alternative or addition to the polysaccharide gum is a polyacrylic acid polymer. A common variety of polyacrylic acid polymer is known generically as "Carbomer" that are polyacrylic acid polymers lightly cross-linked with polyalkenyl polyether. There materials are commercially available from the B. F. Goodrich Company (Akron, Ohio) under the designation "CARBOPOL®". A particularly preferred variety of carbomer are those designated as "CARBOPOL® 940" and "CARBOPOL® 934".

Other polyacrylic acid polymers suitable for use in practicing this invention are those commercially available under the designations "Pemulen®" (B. F. Goodrich Company) and "POLYCARBOPHIL®" (A. H. Robbins, Richmond, Va.). The Pemulen® polymers are copolymers of C10 to C30 alkyl acrylates and one or more monomers of acrylic acid, methacrylic acid or one of their simple esters cross-linked with an allyl ether of sucrose or an allyl ether of pentaerythritol. POLYCARBOPHIL® is a polyacrylic acid cross-linked with divinyl glycol.

The levels and incorporation of polymeric thickeners into the formulations are based on the well-established pharmaceutical principles. Other formulation components such as penetrants, coloring agents, antioxidants, emollients, glidants, and antimicrobials can also be added.

It is also to be understood that in therapeutic formulations the active oxidized carbon nanoparticulate materials can be dispersed, dissolved, emulsified, suspended, lyophilized, encapsulated, micronized, nanoparticulated and the like. In addition, the formulations can contain solvents such as alcohols, polyols, esters, water; thickening and consistency modulating agents such as galactomannan gums, carbohydrate polymers such as starch, cellulose derivatives, alginic acid and derivatives, alkyl acrylate polymers and copolymers, polyvinyl alcohol and derivatives; film forming agents such as cellulose ethers, carbomers; chelating agents, emulsifying agents such as long chain fatty acids, regular or fatty alcohols, and or esters; amino acids, and buffering agents.

In yet a further embodiment, a contemplated oxidized carbon nanoparticulate material composition is formulated as a nasal spray or as an inhalant for administering the active oxidized carbon nanoparticulate material to the lungs or via the cribiform plate to the brain. Compositions for such uses are generally less viscous than those for topical application, and have a water-like viscosity at the temperature of the mammalian subject's body.

In administration by nasal spray, oxidized carbon nanoparticulate materials are delivered by inhalation; for example, oxidized nanoparticulate materials or oxidized carbon nanoparticulate materials that are derivatized with PEG or a chelating agent, or both, can be prepared for dry dispersal, for example, by lyophilization or spray drying a solution containing conjugate, e.g., using methods as described in U.S. Pat. Nos. 6,509,006; 6,592,904; 7,097,827; and 6,358,530. Exemplary dry powder excipients include a low molecular weight carbohydrates or polypeptides to be mixed with the oxidized carbon nanoparticulate materials to aid in dispersal.

Typically, compositions are prepared as injectables, either as liquid solutions or suspensions; solid forms suitable for solution in, or suspension in, liquid vehicles prior to injection can also be prepared. Notwithstanding the preference for an injectable preparation, a topical, nasal spray, or powdered composition also can be dispersed, emulsified or encapsulated in liposomes or micro particles such as polylactide, polyglycolide, or copolymer. [Langer, (1990) *Science* 249(4976):1527-1533.]

In addition to oxidized carbon nanoparticulate material, a contemplated liposome can contain one or more of a sterol; a phosphatidylethanol-amine having fatty acid moieties of 12-18 carbons, a phosphatidylcholine having fatty acid moieties of 12-18 carbons. More specifically, liposome components can be comprised of phosphatidylserine, phosphatidyl-inositol, sphingomyelin, cardiolipin, phosphatidic acid, cerebrosides, dicetylphosphate, dipalmitoyl-phosphatidylglycerol, stearylamine, dodecylamine, hexadecylamine, acetyl palmitate, glycerol ricinoleate, hexadecyl stearate, isopropyl myristate, amphoteric acrylic polymers, fatty acid, fatty acid amides, diacylglycerol, diacylglycerolsuccinate, DMPC (1,2-dimyristoyl-sn-glycero-3-phosphocholine), or DMPG (1,2-dimyristoyl-sn-glycero-3-phospho-rac-[1-glycerol]).

In alternative embodiments, types of pharmaceutical excipients that are useful as carriers for dry powder dispersal include stabilizers such as human serum albumin (HSA), that is also a useful dispersing agent, bulking agents such as carbohydrates, amino acids and polypeptides; pH value adjusters or buffers; salts such as sodium chloride; and the like. These carriers can be in a crystalline or amorphous form or may be a mixture of the two. Devices that can be used to deliver powder or aerosol formulations include those as described e.g., in U.S. Pat. Nos. 5,605,674 and 7,097,827, for example, the devices can be nebulizers.

The oxidized carbon nanoparticulate material and their formulations used to practice the uses and methods as provided herein can also be lyophilized. Thus, a stable lyophilized pharmaceutical composition as provided herein can be made by lyophilizing a solution comprising oxidized carbon nanoparticulate material alone or admixed with a bulking agent, e.g., mannitol, trehalose, raffinose, and sucrose or mixtures thereof. There are many other conventional lyophilizing agents. Among the sugars, lactose is the most common. Also used are citric acid, sodium carbonate, EDTA, benzyl alcohol, glycine, sodium chloride, etc. [See for example, Baheti et al., (2010) *J Excip Food Chem* 1(1):41-54.]

In addition, sterile, fixed oils are conventionally employed as a solvent or suspending medium. For this purpose, any bland fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful.

A mammal in need of treatment (a subject) and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain the water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

Chemotherapeutic Agents

A contemplated composition can include a chemotherapeutic agent along with an oxidized carbon nanoparticulate. These chemotherapeutic agents can comprise an alkaloid; covalent DNA-binding agent; noncovalent DNA-binding agent; antimetabolite; enzyme; hormone; platinum compound; monoclonal antibody conjugated with anticancer a drug, toxin, and/or radionuclide; biological response modifier; hematopoietic growth factor; inhibitor of angiogenesis; DNA cross-linking agent; topoisomerase I inhibitor; or microtubule inhibitor. By way of even further example, chemotherapeutic agent can be 2-chlorodeoxyadenosine, 2'-deoxycoformycin, 2'-deoxycoformycin, 5-fluorouracil, 5-fluorodeoxyuridine, 4-dimethoxydaunomycin, 11-deoxydaunorubicin, 13-deoxydaunorubicin, adriamycin-14-benzoate, adriamycin-14-octanoate, adriamycin-14-naphthaleneacetate, 6-mercaptopurine, 6-thioguanine, acyclovir, amsacrine, anastrozole, asparaginase, azathioprine, busulfan, camptothecin, canbusil, carboplatin, carminomycin, carmustine, chlorambucil, chlorodeoxyadenosine, cisplatin, cyclophosphamide, cytarabine, dactinomycin, dacarbazine, daunorubicin, doxorubicin, docetaxel, doxorubicin, epirubicin, etoposide, fludarabine, flutamide, hydroxymethylmelamine, idarubicin, ifosphamide, isirinotecan, lomustine, lovastatin, mechlorethamine, melphalan, methotrexate, mithoxanthrone, mitocycin, oxalaplatin, semustine, thiotepa, tamoxifen, taxol, taxotere; teniposide, thioguanine, topetecan, vincristine, vinblastine, and vindesine.

EXAMPLES

The following examples present a description of various specific aspects of the intended invention and are not presented to limit the intended invention in any way.

Example 1—Materials and Methods

Unless otherwise stated, all chemicals were purchased from Sigma-Aldrich and used without further purification unless otherwise stated. Single-walled carbon nanotubes (SWCNTs; Batch HPR 187.4) were obtained from the HiPco Laboratory at Rice University. GMP AC was obtained from EnviroSupply & Service. Fuming (90%) nitric acid was obtained from Alfa Aesar.

Other suitable PEGylated or functionalized carbon nanomaterials can be used, including, but limited to PEGylated graphite oxide nanoribbons (PEG-GONR), PEGylated oxidized carbon black (PEG-OCB), and PEGylated carbon black (PEG-CB), are also contemplated.

The nanomaterials can be manufactured from various commercially available carbonaceous starting materials using established synthetic methods. The synthesis and characterization of PEG-HCCs can be found in Berlin et al. (2010) *ACS Nano.* 4(8):4621-4636, whose disclosures are incorporated herein by reference. The synthesis and characterization of PEG-OACs are listed in Example 3.

Example 2: Nanozyme Materials

Nanozymes, catalytic nanoparticles can perform various chemical reactions in a nonstoichometric manner. In this example, the nanozymes are derived from oxidized carbon nanomaterials comparable to PEG-HCCs (sub-40 nm in size, highly conjugated planar graphene domains and optimal balance of oxygen-containing moieties). The existing nanozymes derived from oxidized carbon nanomaterials have been shown to effectively dismutate superoxide (SO), and catalyze the reaction of mitochondrial substrates such as nicotinamide adenine dinucleotide:cytochrome c oxidoreductases.

Carbon nanoparticles (CNPs) rich with $sp^2$-hybridized carbons, decorated with oxygen-containing moieties function as nanozyme catalysts for the dismutation of superoxide and transport of electrons in the mitochondria. PEG-HCCs catalytically dismutate superoxide via a two-step reaction that has a total activation energy lower than the spontaneous dismutation of SO alone. This process takes place by the oxidation of SO to $O_2$ and concomitant reduction of the PEG-HCC. In the second step, SO is reduced to $H_2O_2$ by the PEG-HCC. This process takes place because of the relative ease by which PEG-HCCs accept and donate electrons (6, 16).

The driving force for alternative carbon sources is the elimination of the dependence on single-walled carbon nanotubes (SWCNTs) as the starting material since, in addition to their expense, they are considered toxic. We have seen no toxicity whatsoever following their harsh oxidation to much smaller and non-tubular HCCs. Although effective CNPs were developed, from bituminous coal from the prior cycle, the variability of the source material can potentially complicate clinical translation.

In this application, CNPs with similar and different properties compared to HCCs are synthesized, starting from material made using good manufacturing practice (GMP) activated charcoal, by tailoring the oxidation of the particles to attain an optimal balance of oxygen-containing moieties for improved antioxidant and mitochondrial activity. The nanozyme candidates address the concerns of SWCNT.

The GMP-sourced activated charcoal (AC) continues to be, however, a safe and inexpensive candidate to form oxidized activated charcoal (OAC). Low ash content activated coal derived from NSF/ANSI certified processed bituminous coal can serve as an alternate source of activated material, activated coal.

Figure 2:
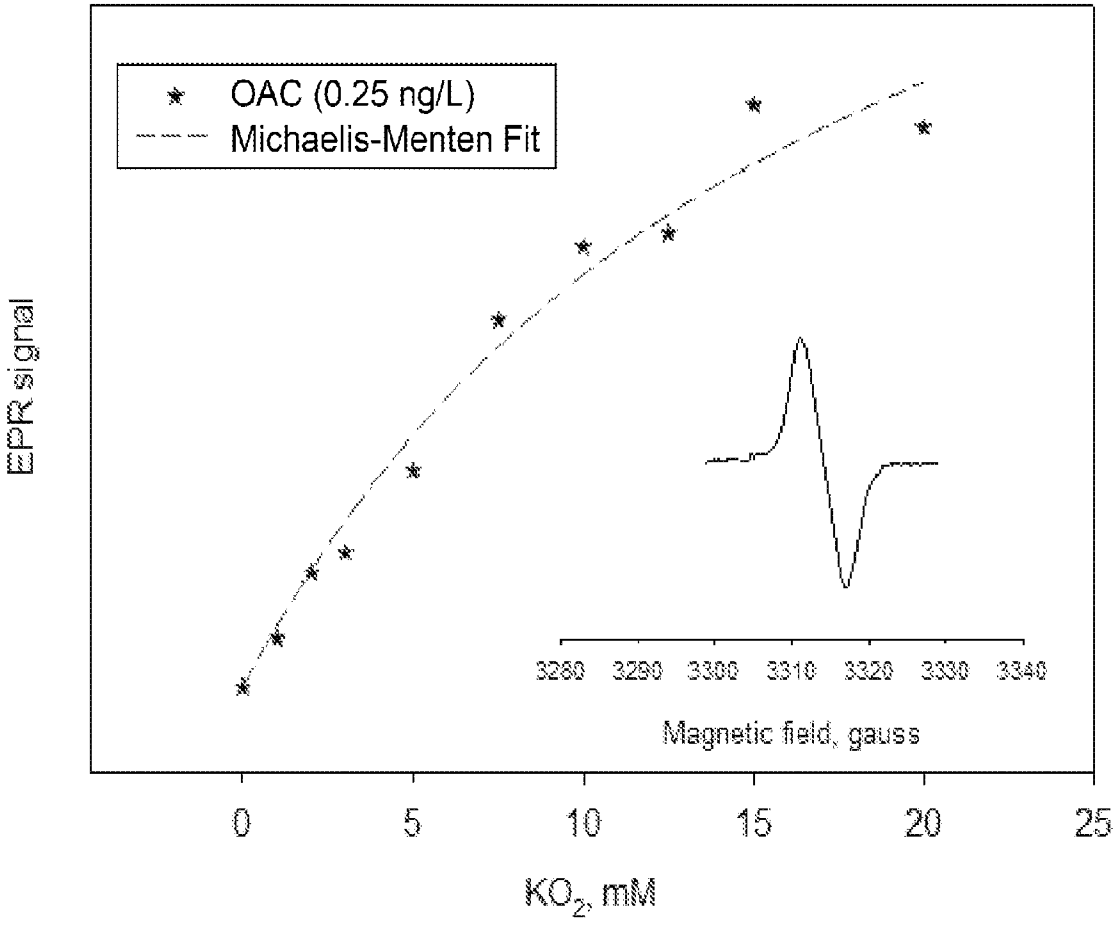
FIG. 2 Shows a plot of electron paramagnetic resonance (EPR) signal vs. $K_2O$ concentration of PEG-OAC present at 0.25 ng/L (stars); A dashed fit line through the measurements is a Michaelis-Menten saturation curve that indicates enzyme-like catalytic activity of the nanoparticle. Included is an insert that shows a stable radical is confirmed.

OAC like a HCC or a PEG-HCC analog contains: (1) a highly conjugated carbon core; (2) a balance of oxygen-containing functional groups, particularly 1,2-quinones at the edges for preferred electrochemical activity, and carboxylic acids for facile addenda attachment such as PEGylation; (3) a biologically compatible size approximately in the sub-100 nm size range, such as the particles of Example 3, down to an average diameter of 2.8 nm as shown in FIGS. 15 and 16; and (4) the ability to catalytically dismutate superoxide (FIG. 2). An additional property of preferred OACs not present in HCCs is that OACs are stably-dispersible in water as is discussed hereinafter and shown in FIG. 6.

Thus far, we have developed promising PEG-HCC replacements from bituminous coal-derived graphene-derived quantum dots (GQDs) and OAC. We have published several papers on coal-derived GQDs, (27, 28) and oxidation and PEGylation to generate PEG-GQDs as antioxidants (17) and neuroprotectants (7). Quinones were identified as central in the redox activity of HCCs (8); therefore, a balance must be maintained between the quinone groups and other oxygen-containing functionalities. Oxidation of AC can be optimized for quinone and carboxylic acid. Ultimately, preparation of a particle with electrochemical characteristics mimicking those of the PEG-HCCs is the most desired outcome.

PEGylation reactions are typically carried out as described in U.S. Pat. No. 9,572,834 and described in greater detail in Berlin et al., ASC Nano 2010; 4:4621-4636. Broadly, 5000 MW methoxy-(polyethylene glycol)amine was coupled to the carboxy groups of the OAC particles to form amides using N,N'-dicyclohexylcarbodiimide (DCC), 4-dimethylamino-pyridine (DMAP) in dimethyl formamide (DMF). Similar materials are prepared using other coupling chemistries and also by reaction of the particles' ketone functionalities with the same amine in the presence of a reducing agent such as sodium cyanoborohydride and the like.

Figure 3:
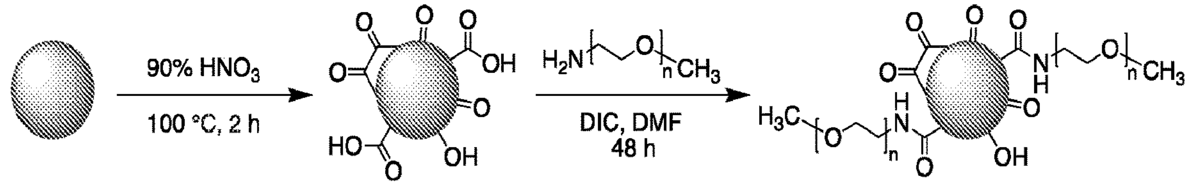
FIG. 3 shows a schematic alternative synthesis of PEG-OAC. Here, GMP AC is oxidized via fuming nitric acid (no oleum used in this scheme as used for PEG-HCC) followed by PEGylation.

PEG-OAC is synthesized by reacting the AC with 90% $HNO_3$ at about 100 to about 140° C. for 1-24 hours, varying oxidation conditions and time (FIG. 3). These particles have been used as prepared. It is contemplated that the reaction will occur in sub-1 hour time periods in a flow reactor device. It is also contemplated that the activated charcoal particles will be made more homogeneous in size to being on the average about 20 nm as by vigorous shaking prior to reaction to yield more homogeneously sized OAC particles.

Each batch is subjected to quality control and characterized to determine electrochemical activity by cyclic voltammetry (CV), oxygen-containing functionalities by X-ray photoelectron spectroscopy and Fourier-transform infra-red spectroscopy (XPS and FTIR), PEGylation efficiency by thermogravimetric analysis (TGA), size by high-resolution transmission electron microscopy (HRTEM), particle height profile by atomic force microscopy (AFM), hydrodynamic volume by dynamic light scattering (DLS) or nanoparticle tracking analysis (NTA), and acceptable trace metal level by inductively coupled plasma mass spectrometry (ICP-MS).

To alleviate concerns of metal contamination (as previously seen with graphene oxide (GO) (31, 32)), all materials are subjected to previously described filtration methods (17). Trace metal analysis by ICP-MS is performed to as reported (32). Published guidelines are followed to minimize endotoxin (33). The MIRIBEL criteria are followed to insure both biological relevance and reproducibility (34).

If the OAC have a highly conjugated carbon core, oxygen-containing functionalities that result in a broad reduction potential with a high onset potential, and a compatible size in the sub-100 nm size (diameter) range such as about 1 to about 40 nm, or about 3 to about 30 nm, those particles that pass through a 0.22 μm filter, display both antioxidant, enhancement of generation of persulfides and/or polysulfides, and electron transfer shuttling properties in solution, in cells and in vivo.

Oxidized carbon nanoparticles (CNPs) can be heterogeneous. To minimize variation, each synthesis is performed in triplicate to establish expected mean and standard deviation values for target factors listed above.

OACs are typically disk-shaped and have diameters of about 1 to about 30 nm that can vary depending on reaction conditions. As disks, particles would be round. However, not all particles are round and rather have a flattened oblong shape. The longest dimension of the latter particles is deemed herein to be the diameter of those particles.

Shape-effects can alter the nanomaterial's ability to permeate the cell membrane and necessitates further investigation, as the wider, disk-like shape of OAC can potentially hinder cellular uptake compared to the thinner, ribbon-like HCCs (2). However, a possible shape effect can be less important after PEGylation because the PEG moieties form a micelle-like structure around the hydrophobic conjugated carbon core of the nanomaterials. The diameter can also influence cellular uptake and subcellular distribution with the mitochondria as an example, with the ideal size and shape dependent on the pathology being targeted. Graphene quantum dots (GQDs) can also be used. Although they were prepared from a variegated source material, they are effective in the TBI model examined.

Figure 4:
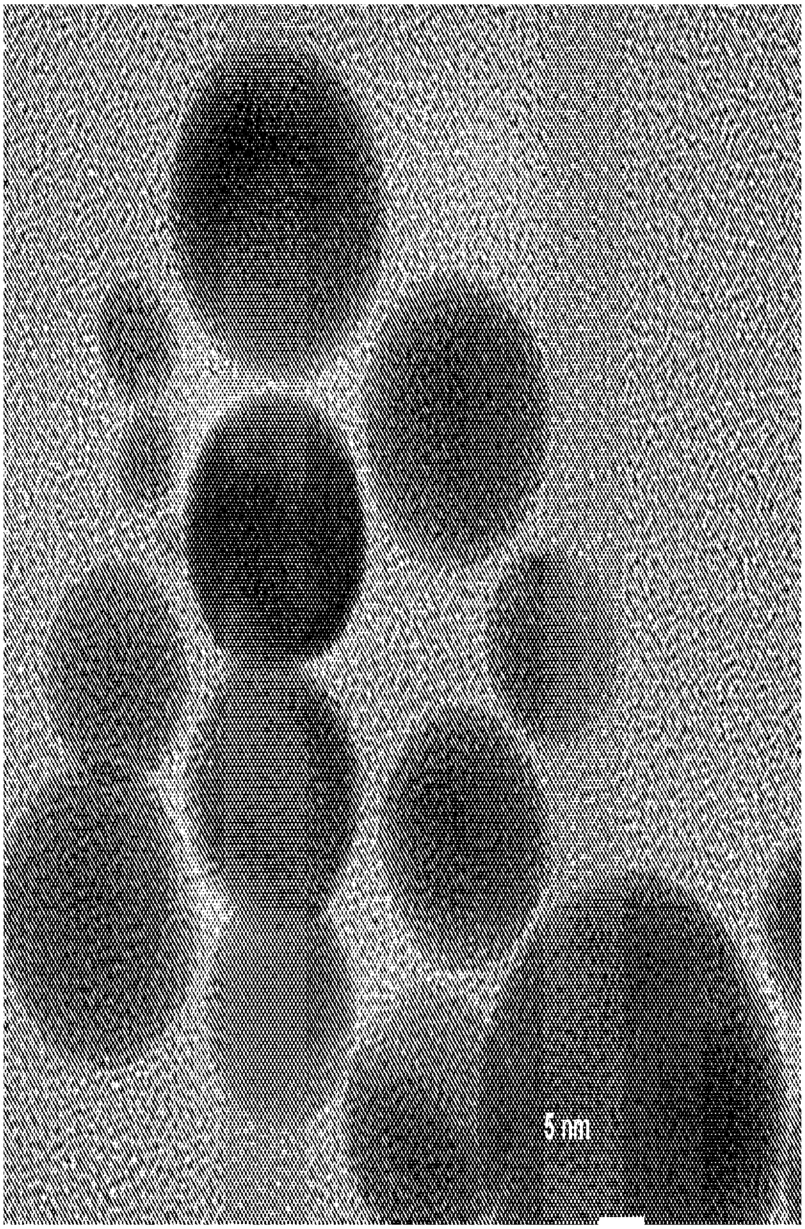
FIG. 4 is a photomicrograph showing as-synthesized OAC particles visualized by transmission electron microscopy. Scale bar is 5 nm.

The analytical techniques employed were as reported in the cited references (16, 35), which are specifically incorporated herein by reference for this purpose. CV is collected as reported (16). XPS is used to acquire high resolution spectra for elemental analysis of carbon-containing functional groups using X-Ray emission from the carbon is electron orbital. high resolution spectra for elemental analysis as described (17). FTIR is acquired for analysis of oxygen-containing functionalities. AFM is employed for measuring particle height profiles, and HRTEM is used for lateral shape determination as described (FIG. 4) (27).

CNPs are assessed for toxicity for each tested cell line, and cytotoxicity is based on a minimum 10-fold higher concentration without 10% or greater cell loss. Only those iterations that do not demonstrate toxicity in vitro advance in vivo.

Example 3—Uniqueness of the Biological Process of Oxidation of Activated Charcoal by Nitric Acid The present example demonstrates a new synthesis method for producing an oxidized carbon nanomaterial that provides for a biologically active oxidized carbon nanoparticle product without added substituents such as solubilizing polymers. Synthesis methods using other techniques resulted in non-biologically active preparations of oxidized carbon materials, thus rendering these materials not useful for use in a composition for reducing reactive oxygen species in vivo or for treatment of diseases/pathologies associated with these conditions.

In this example, the oxidized carbon material used was GMP activated charcoal (AC). However, any other carbon material can be used with an expected similar result.

The AC was oxidized via $HNO_3$ to synthesize oxidized activated charcoal (OAC). Typically, in the existing literature relevant to non-biological hydrocarbon work with oxidized graphene-like materials, oxidation occurs with non-fuming nitric acid (70% $HNO_3$). The present work in biological settings requires much higher concentrations, in this case, fuming (90%) nitric acid. In the present study, it is shown that this is a key difference between biological and non-biological applications.

Figure 5:
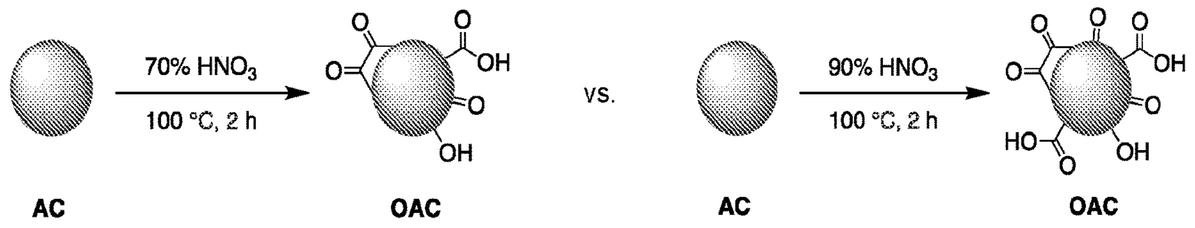
FIG. 5 is a schematic depiction of a synthesis scheme for oxidized activated charcoal (OAC) by nitric acid. Left panel is the synthesis used in prior work to generate a sensor (not in-vivo or in cells). Right panel is the synthesis scheme to prepare the oxidized activated charcoal for in-vivo and cellular use.

To determine whether the strength of the oxidant affected the characteristics of the product, AC was subjected to oxidation by either 70% $HNO_3$ or 90% $HNO_3$ (FIG. 5). The resulting OAC products were analyzed by TGA, XPS, and CV to delineate the differences between the materials.

Figure 6:
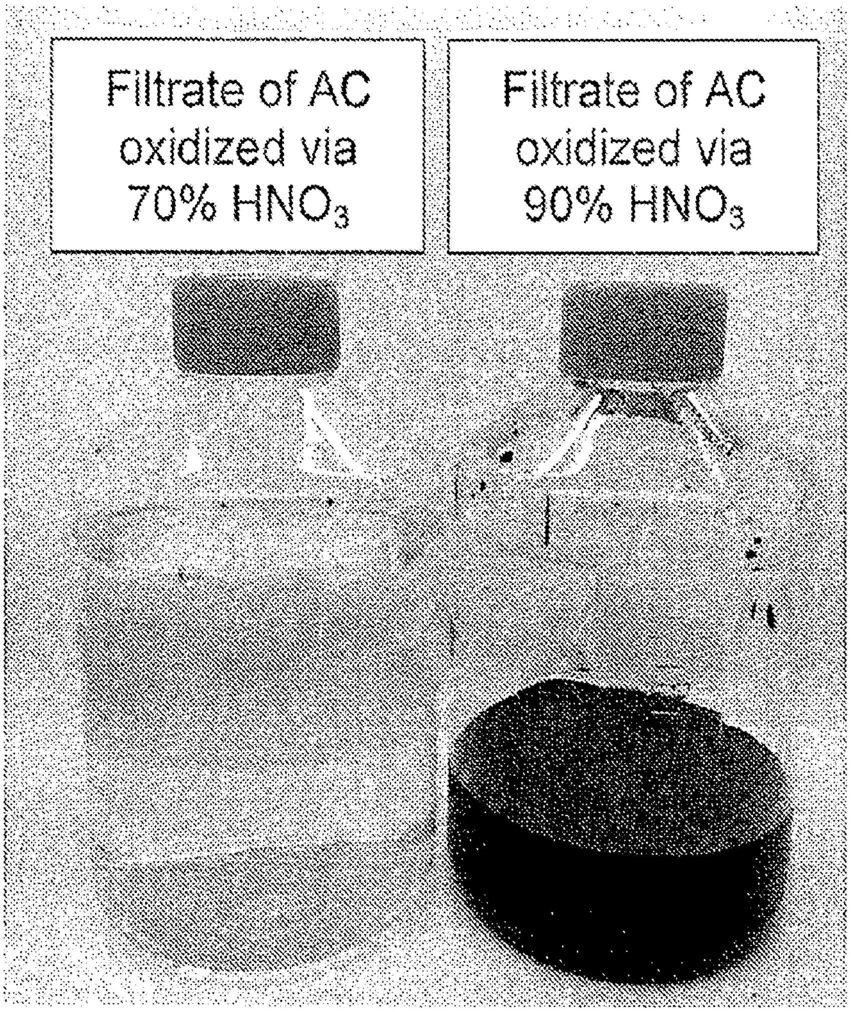
FIG. 6 is a photograph of the filtrates of AC oxidized via 70% $HNO_3$ (left) and via 90% $HNO_3$ (fuming nitric acid; right). It is noted that OAC oxidized using 90% $HNO_3$ results in a water-dispersible product that is able to pass through a 0.22 μm PES filter. The product resulting from the synthesis of OAC using 70% $HNO_3$ is insoluble in water and remains on the filter membrane, hence the clear solution.

Characterization of OAC Synthesized Via Varying Oxidant Strength:

The most notable difference between OAC synthesized using 70% $HNO_3$ vs. 90% $HNO_3$ is the water dispersibility of the resulting oxidized activated charcoal nanoparticulate material (FIG. 6). The 90% $HNO_3$-oxidized AC product is completely water-dispersible and is capable of passing through a 0.22 μm PES filter, whereas the 70% $HNO_3$ oxidized AC product is insoluble in water and does not pass through the filter (FIG. 6). This result is likely due to the harsher oxidizing conditions leading to smaller particles with a higher oxygen content.

Figure 7:
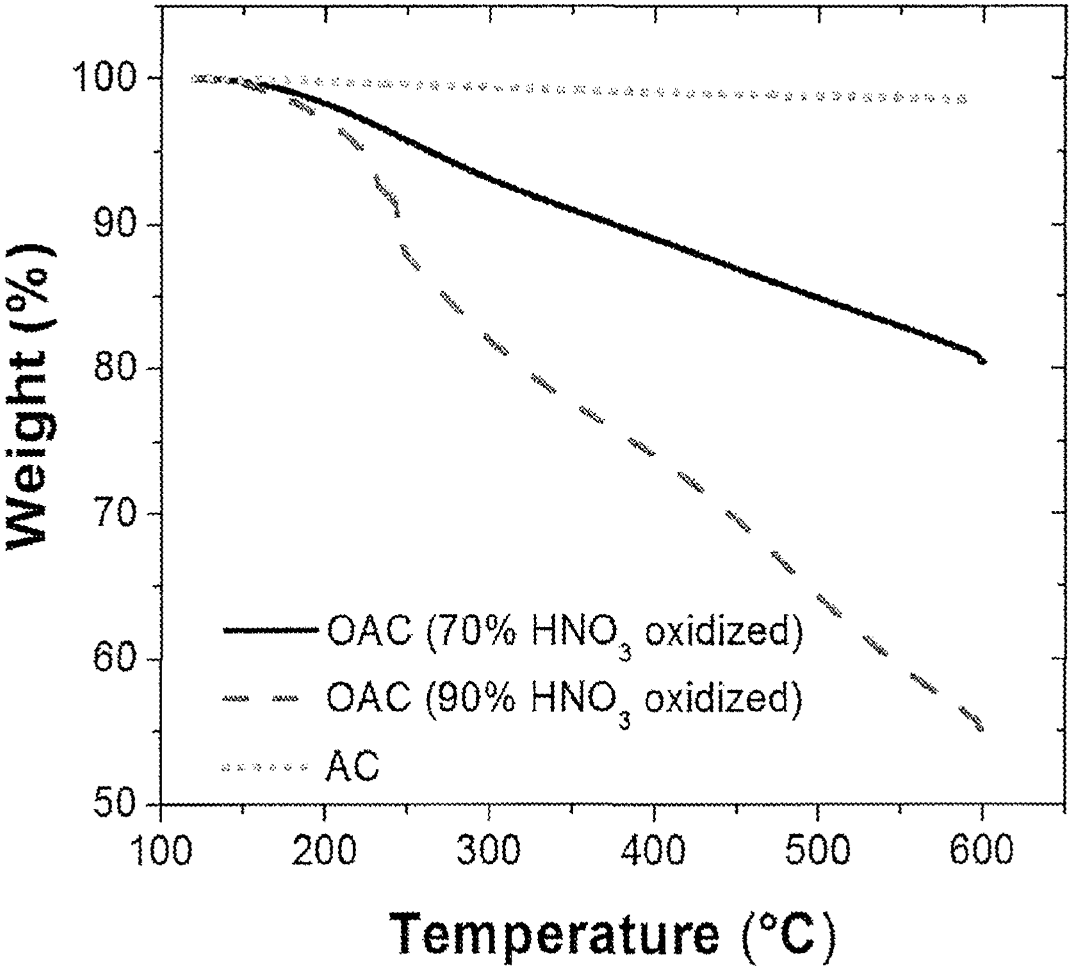
FIG. 7 is a graph showing thermogravimetric analysis (TGA) of activated charcoal (AC), OAC oxidized by 70% $HNO_3$, and OAC oxidized by 90% $HNO_3$ showing weight losses of 1.5%, 19.5%, and 45%, respectively. The OAC synthesized using 90% $HNO_3$ displays the highest weight loss, indicating the material is more sufficiently oxidized. The measurements were acquired under $N_2$ at a ramp rate of 10° C./minute until 600° C.

Analysis by TGA indicated the 90% $HNO_3$-oxidized OAC was more effectively oxidized due to the higher weight loss around 190° C. to 210° C. (the temperature range at which oxygen-functionalities decompose) compared to the activated charcoal parent material and the 70% $HNO_3$ OAC (FIG. 7). Although the XPS analysis does not show a significant difference between the oxygen-containing functionalities of the two OAC materials, the 90% $HNO_3$ oxidized product does have a carbonyl content that is almost double that of the 70% $HNO_3$ oxidized product (Table 1, below).

Figure 8:
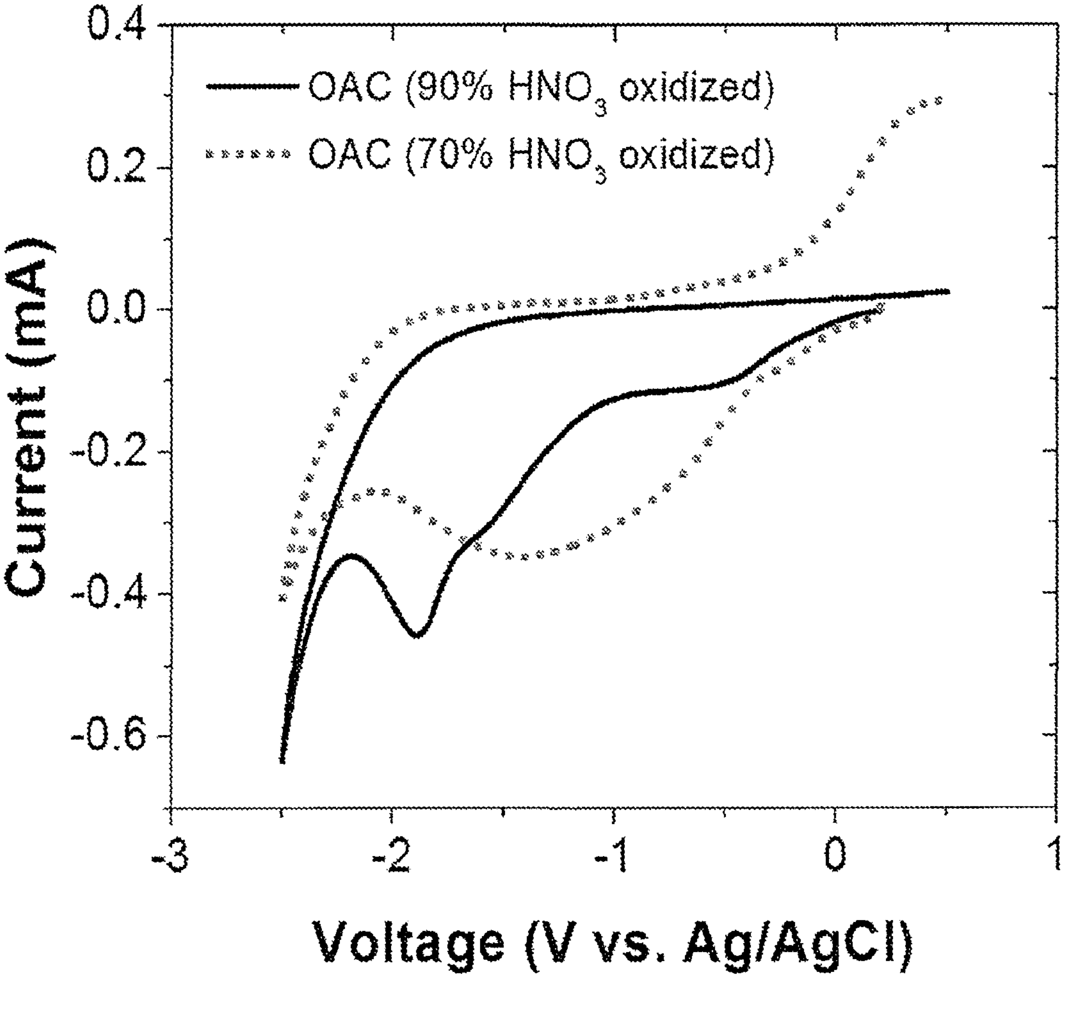
FIG. 8 is a plot of current in milliamps (mA) vs. volts that illustrates the electrochemical activity of OAC synthesized via oxidation with 90% $HNO_3$ compared to OAC synthesized via oxidation with 70% $HNO_3$. Both materials display onsets to the reduction potential >0 V (approximately +0.2 V); however, the reduction potential of the 90% $HNO_3$ oxidized material has various shoulder peaks whereas that of the 70% $HNO_3$ material is a single broad peak.

Of the carbonyl moieties, the 1,2-quinone groups are of primary interest as aromatic quinone-type moieties display reduction potentials with higher onsets than hydroxyl or carboxyl functionalities. Therefore, the presence of quinone groups is important for the electrochemical activity of the OAC materials. Although the 90% $HNO_3$ OAC shows a higher carbonyl atomic percent, the onsets to the reduction potentials of both OAC products are comparable (approximately +0.2 V) (FIG. 8).

TABLE 1

XPS analysis of OAC (C 1s peak deconvolution) in %

| Functional group | OAC Synthesized Using 70% $HNO_3$ | OAC Synthesized Using 90% $HNO_3$ |
|---|---|---|
| C═C/C—C | 59.7 | 53.9 |
| C—O—C/C—O | 15.3 | 13.6 |
| C═O | 6.2 | 11.0 |
| O—C═O | 18.9 | 17.3 |

The presence of 1,2-quinone groups also provides a means of preparing ethylenediamine derivatives of oxidized carbon nanoparticulate materials. Exemplary ethylenediamine-blocked PEG-HCCs [EN-PEG-HCC] or non-pegylated OAC can be prepared as shown schematically below.

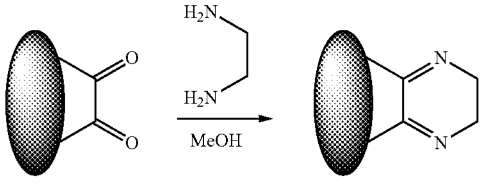

PEG-HCC EN-PEG-HCC

In an illustrative synthesis, an aqueous solution of PEG-HCCs (5.0 mL, 1.2 mg/mL, 6 mg) was added to ethylenediamine (5.0 mL, 4.5 g, 75 mmol). Water was removed via the rotovap, leading to precipitation of the PEG-HCCs in ethylenediamine. MeOH (6 mL) was added to disperse the PEG-HCCs, along with molecular sieves.

The reaction was stirred at room temperature for 5 days before dilution in DI $H_2O$ and filtration by a 0.22 μm polyethersulfone (PES) membrane. The material was purified via crossflow filtration (Spectrum® Labs Krosflo®, Research IIi TFF System) with a 50 kDa mPES dialysis column (about 1 atm transmembrane pressure) to yield 15 mL of EN-PEG-HCC with a carbon core concentration of 400 mg/L.

Example 4—Sulfide Oxidation

The present example illustrates the application of carbon nanomaterials in the intracellular synthesis of polysulfides in a manner that exceeds what cells are endogenously capable of and can prove of therapeutic use for treating a variety of injurious conditions including but not limited to: inflammation, sepsis, stroke, and other diseases where free radical generation is implicated as a plurality cause.

Polysulfides are produced endogenously as antioxidants in part by superoxide dismutase (84) and are formed under hypoxia (83). These reactive sulfur species (RSS) are capable of quenching free radicals (81, 84) both in vitro and in materials such as rubber. The catalytic formation of polysulfides has been shown with superoxide dismutase and catalase (87, 91), but to the best of our knowledge has not been shown with an exogenously-supplied catalyst.

Figure 9A:
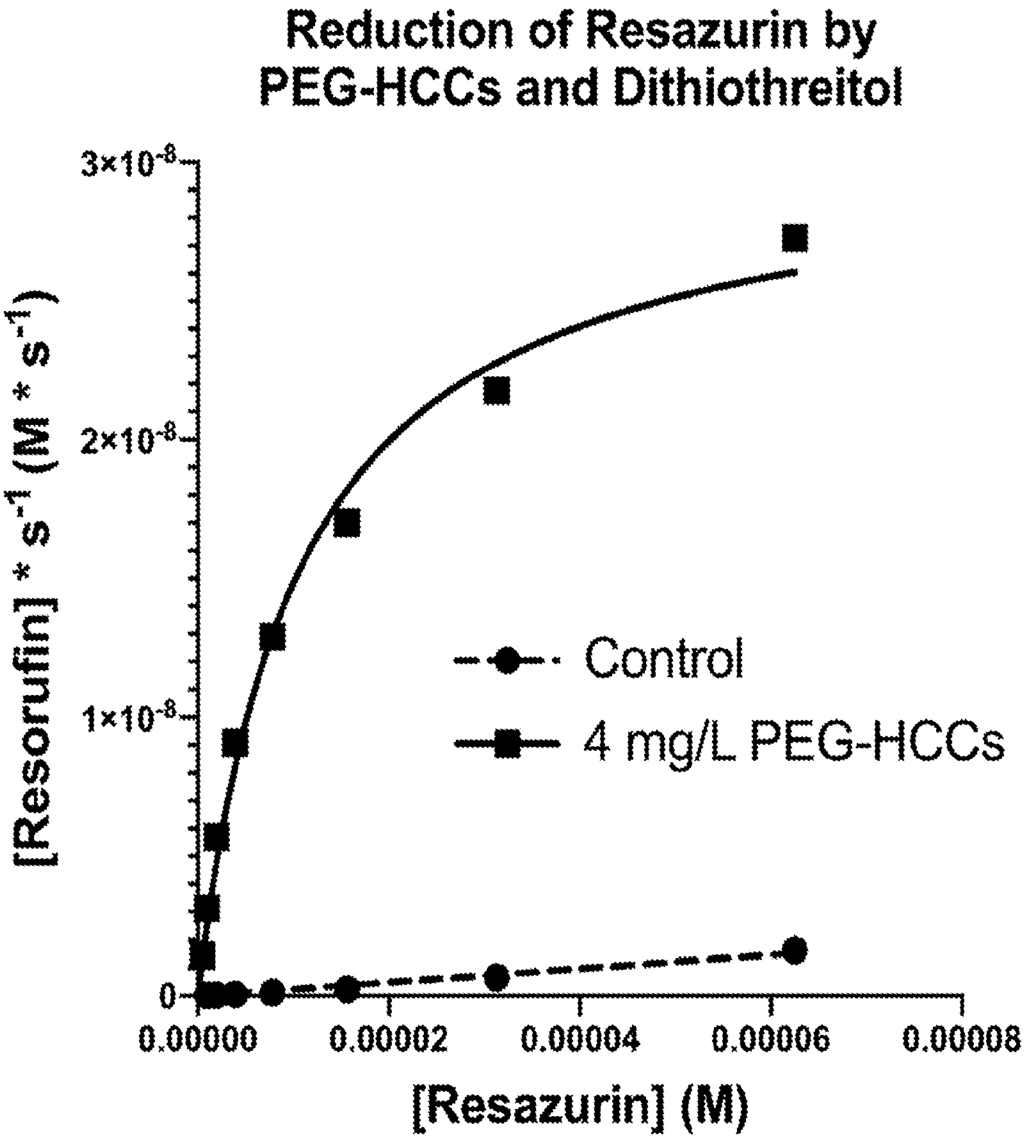
FIG. 9A is a graph showing reduction of resazurin by PEG-HCCs (pegylated hydrophilic carbon clusters) and dithiothreitol as the reductant demonstrating the ability to act as a catalyst for the reduction of resazurin with a different thiol molecule as the reductant. (Control, circles -●-; 4 mg/L PEG-HCCs, squares -■-).
Figure 9B:
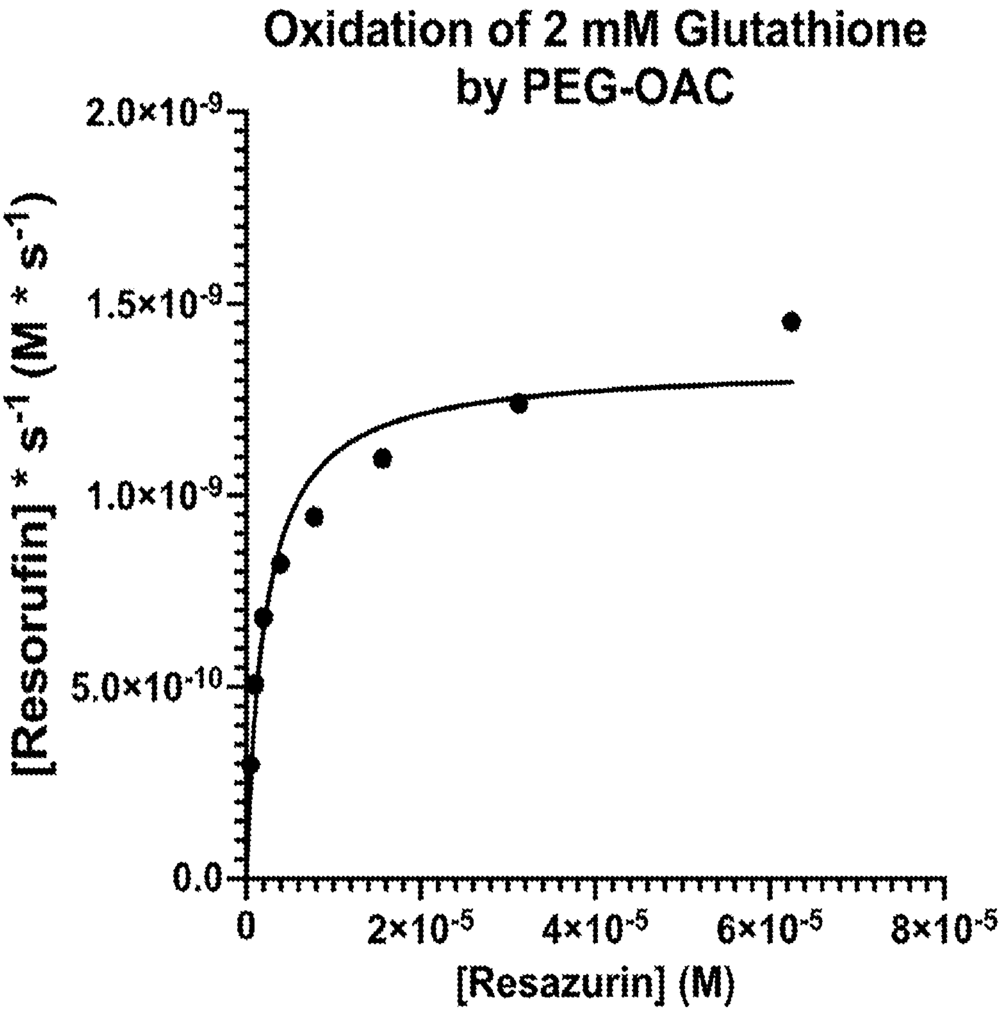
FIG. 9B is a graph showing the catalyzed reduction of resazurin to resorufin by PEG-OAC with 2 mM glutathione as the reductant.
Figure 10A:
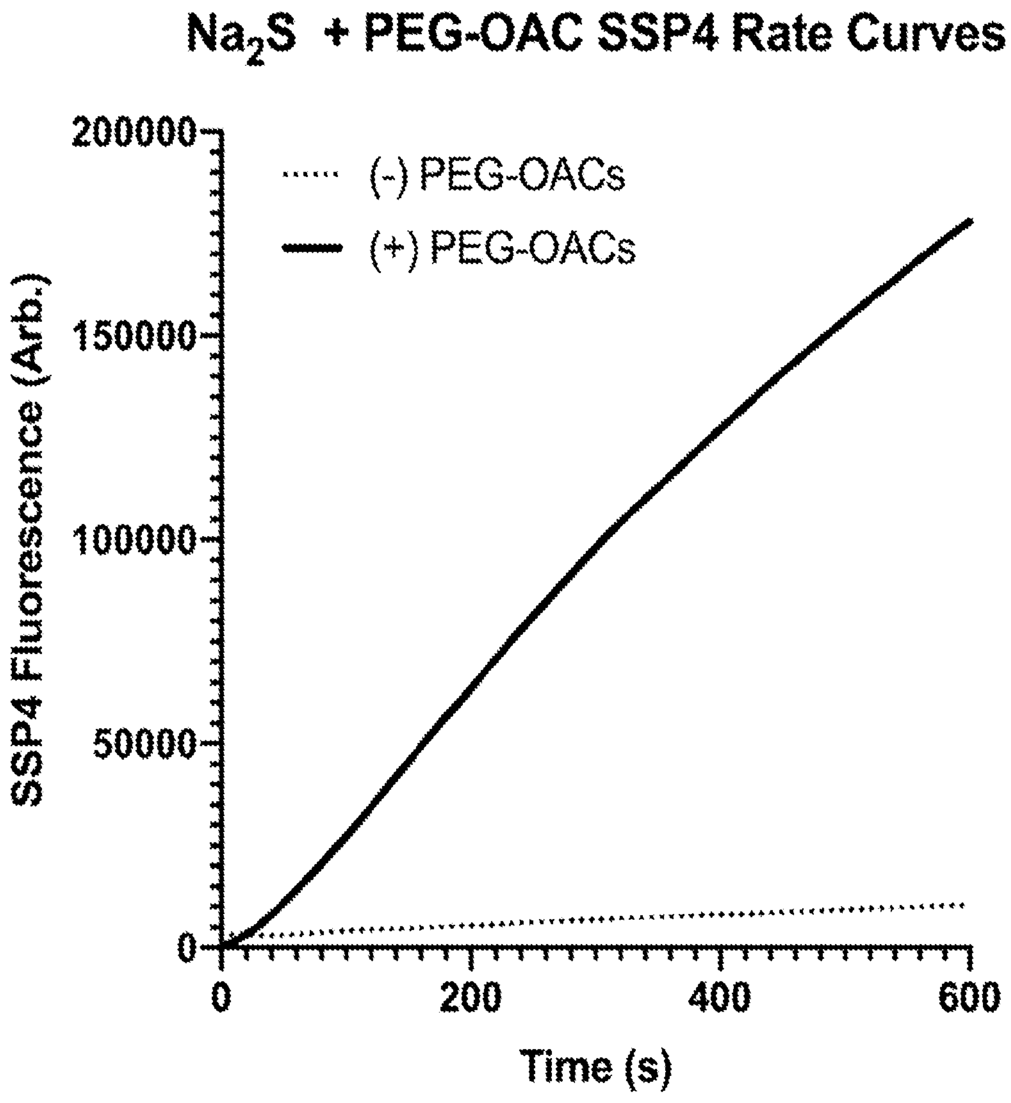
FIGS. 10A and 10B are graphs showing polysulfide preparation from the reaction $Na_2S$+PEG-OAC (FIG. 10A), and PEG-HCC and EN-PEG-HCC (FIG. 10B) in the presence of sulfur sensing probe 4 (SSP4) [discussed in U.S. Pat. No. 10,520,509; available from Dojindo Molecular Technologies, Rockville, MD] and $Na_2S$. Oxidized pegylated, activated charcoal (PEG-OAC, upper line), or without OAC (no nanomaterials, lower line). The PEG-OAC is shown to provide a very effective catalyst of $H_2S$. The PEG-OAC was synthesized from a GMP, medicinal grade source of activated charcoal. The graph demonstrates that the rate of production of polysulfides [3',6'-di(O-thiosalicyl)-fluorescein; sulfane sulfur probe 4; SSP4] measured by SSP4 fluorescence was greatly enhanced in the presence of the PEG-OAC material.
Figure 10B:
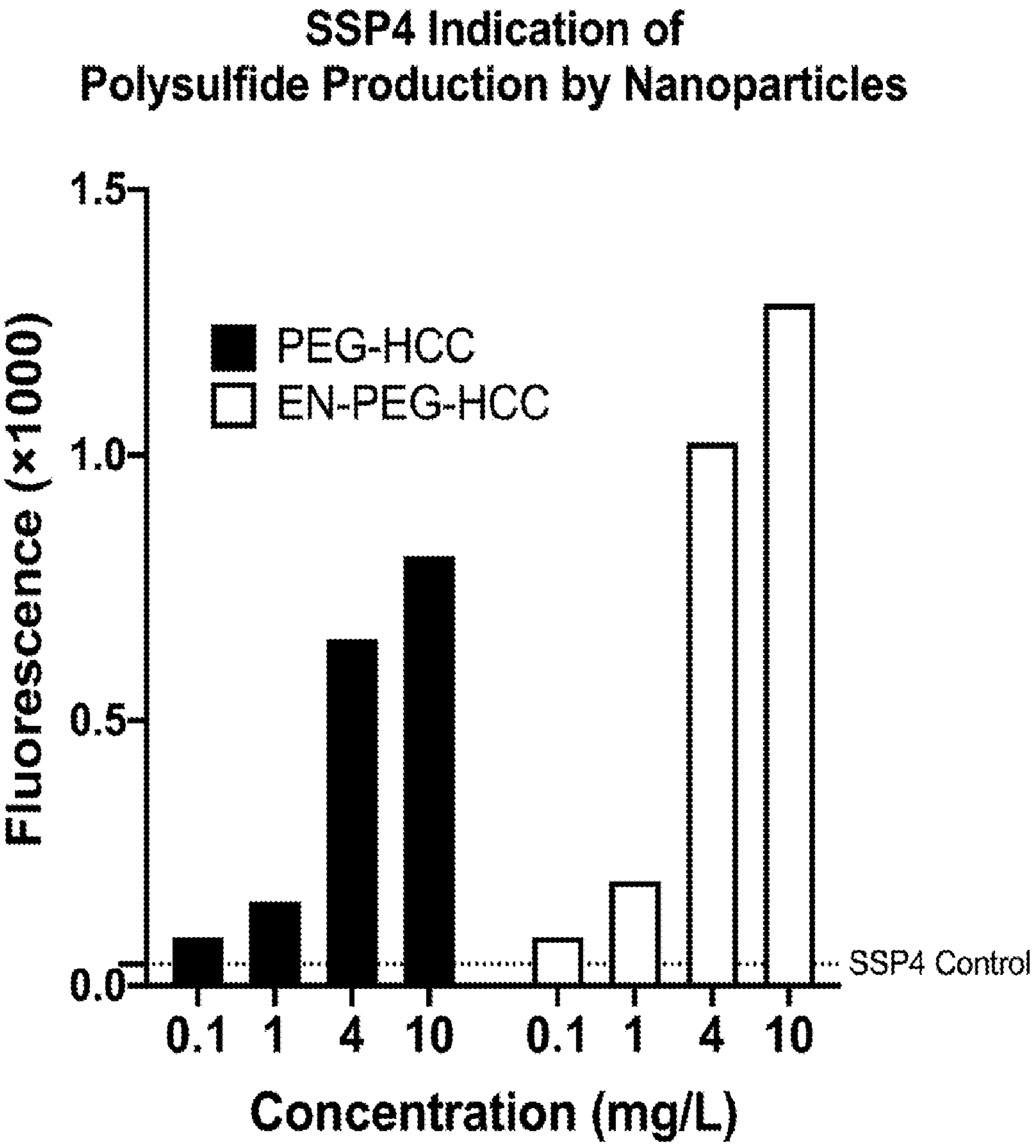
Figure 11A:
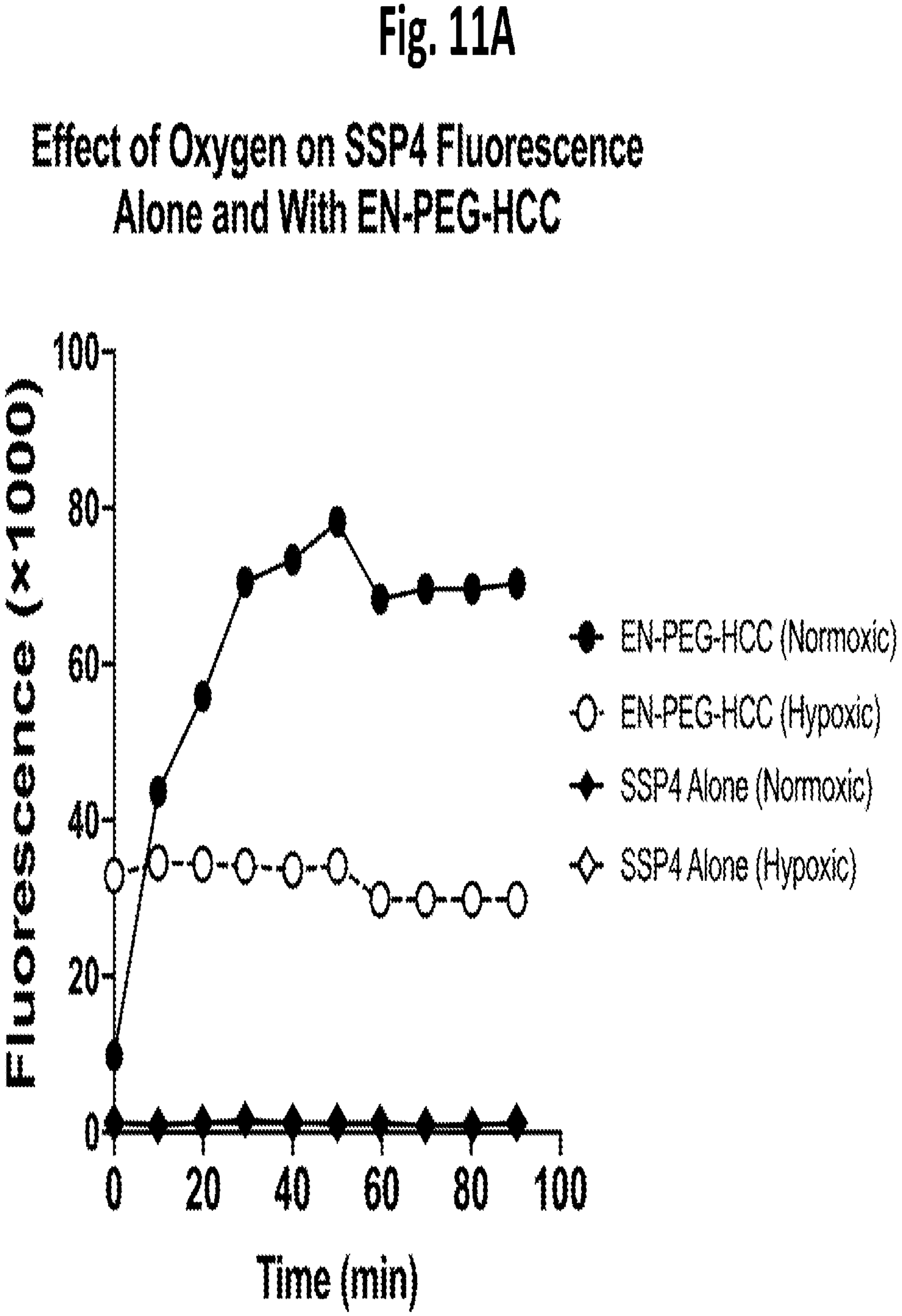
FIGS. 11A and 11B are graphs showing SSP4 fluorescence in cultured b.End3 cells 10 mg/L NPs normoxia vs 90-minute hypoxia (t=0) with EN-PEG-HCC (FIG. 11A) and PEG-HCC (FIG. 11B). Hypoxic samples were incubated in deoxygenated buffer (bubbled with $N_2$ for 30 minutes) with NPs for 90 minutes prior to first reading (t=0), then read for another 90 minutes in room air. Normoxic samples were mixed and read for 90 minutes. EN-PEG-HCC=ethylenediamine-blocked PEG-HCCs. EN-PEG-HCC again demonstrate greater SSP4 production compared to PEG-HCC. SSP4 Alone plots for normoxic and hypoxic atmospheres overlap demonstrating no SSP4 fluorescence increase in the absence of oxidized nanomaterial. EN-PEG-HCC induces SSP4 fluorescence under both hypoxic and normoxic conditions with different kinetics.

The present carbon-based nanozymes (PEG-HCCs, PEG-OACs) have been found to readily oxidize thiols (FIGS. 9A and 9B), and indication of their potential activity on persulfidation and $H_2S$. The aforementioned nanozymes dramatically increase the rate of polysulfide formation in a cell-free setting with sodium sulfide as the $H_2S$ donor (FIGS. 10A and B). Likewise, the intracellular rate of polysulfide formation in several preparations is also shown to be greatly enhanced (FIGS. 11A and B). The many-fold increase in polysulfide production is dependent upon particle preparation. In the example shown in FIG. 11A, PEG-HCCs treated with ethylenediamine [EN-PEG-HCC]proved the most efficacious compared to PEG-HCCs in FIG. 11B.

$$H_3O^+ + 2e^- + HSS^- \rightarrow 2HS^- + H_2O \quad E_0 = -0.23\ V \tag{1}$$

$$OAC\cdot \rightarrow OAC^- \quad E_0 \approx +0.20\ V \tag{2}$$

$$H_2O + 2HS^- + OAC\cdot \rightarrow OAC^- + HSS^- + H_3O^+ \tag{3}$$

A possible mechanism of action is shown in Equations 1-3, above. The reduction potentials of the $HSS^-/HS^-$ and $OAC\cdot/OAC^-$ half-cells are favorable because electrons can be transferred ($E_0$=+0.46 V) from the $HS^-$ anion to the OAC particle. The precise mechanism of this reaction is not currently known. The resulting product, a polysulfide as indicated by the SSP4 studies (FIG. 10A), is presumed to be $HSS^-$.

Under normoxic conditions polysulfides can be attacked by oxygen to form $S_2O_3^{2-}$ as noted in Kleinjan et al., *Water Res* 2005; 39(17):4093-4100:

$$S_x^- + 3/2O_2 \rightarrow S_2O_3^{2-} + (X-2)S^0, \tag{4}$$

or be oxidized by hemeproteins such as hemoglobin (Hb) as discussed by Vivitsky et al., *J Biol Chem.* 2015; 290(13): 8310-8320:

$$Hb(II)\text{-}SSSH + HS^* \rightarrow Hb(II)\text{—}SSH \tag{5}$$

$$Hb(II)\text{-}SSH + O_2 \rightarrow Hb(II)\text{—}SS^*O_2 \tag{6}$$

$$Hb(II)\text{—}SS^*O_2 + H_2O \rightarrow Hb(II)\text{—}SSO_3^- \tag{7}$$

$$Hb(II)\text{-}SSO_3^- + O_2 \rightarrow Hb(III)\text{-}SSO_3^- + O_2^{-*} \tag{8}$$

$$Hb(III)\text{—}SSO_3^- \rightarrow Hb(III) + S_2O_3^{2-} \tag{9}$$

Figure 11B:
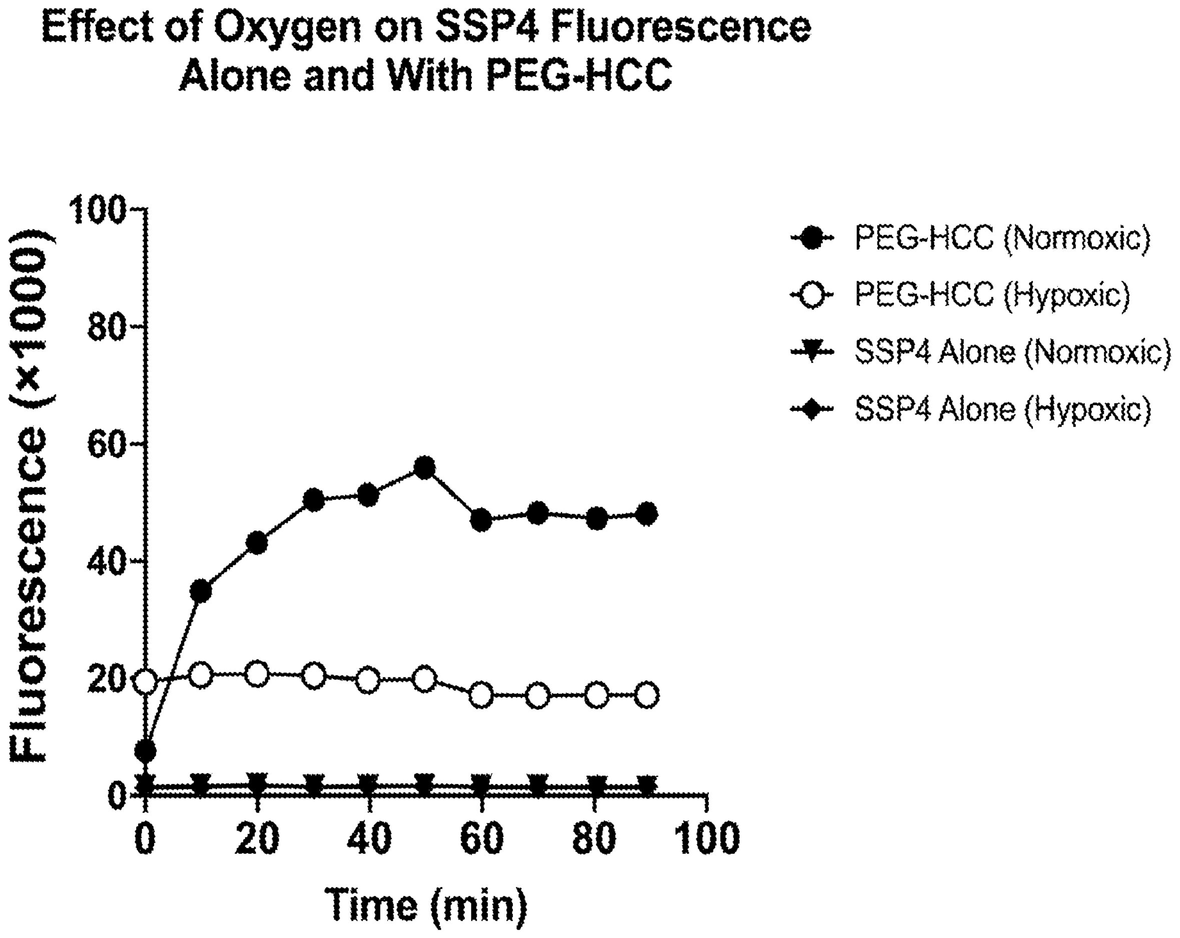

Under normoxic conditions, both PEG-HCCs and EN-PEG-HCCs were shown to catalyze the formation of polysulfides (FIGS. 11A and 11B). However, under hypoxic conditions both EN-PEG-HCCs and PEG-HCCs increased polysulfide yield much faster, making them useful in acute conditions where oxygen deprivation is involved (FIGS. 11A and 11B).

Moreover, it has been found that these nanoparticles function as antioxidants. Specifically, the attachment of an $H_2S$ donor molecule directly to the particle can further enhance the antioxidant and persulfidation properties of the particle as the $H_2S$ source.

The present example provides an illustration of the scope of different known biologically active compounds that can be used as hydrogen sulfide donor skeleton structures in the creation of the modified with a unique R-group, and thereafter be used to facilitate the conjugation of the modified biologically active compound to a linker molecule or to a nanoparticle. Illustrative skeletal groups are illustrated below.

Current methods of sulfide oxidation by carbon-based materials are demonstrated in work described in Powell et al., *Biochem. Pharmacol* (2018), 110-123. Specifically, $H_2S$ donors are classified by their mechanism of $H_2S$ release. Thiol-triggered $H_2S$ donors react with thiols and have a diverse array of reactive moieties with N-benzoylthiolbenzamides, acyl perthiols, polysulfides, dithioperoxyanhydrides, and S-aroylthioxamines filling this category. Two enzyme-triggered structural motifs also exist, germinal-dithiols, and trimethyl locked prodrugs.

Thiolysis

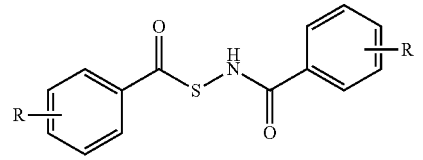

N-Benzoylthiobenzamides

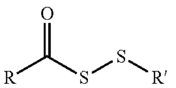

Acyl perthiols

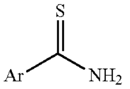

Acyl perthiols

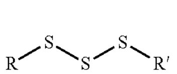

Polysulfides

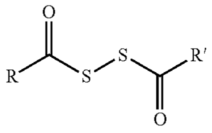

Dithioperoxyanhydrides

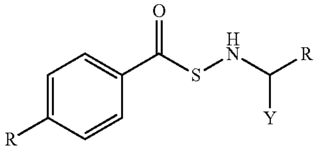

S-Aroylthioxamines

Enzymolysis

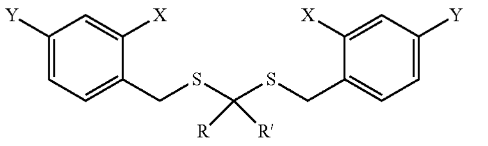

Geminal-dithiols

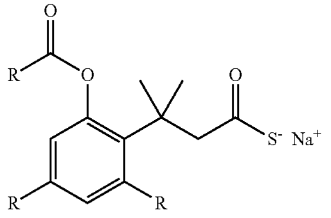

Trimethyl lock prodrug

Figure 12:
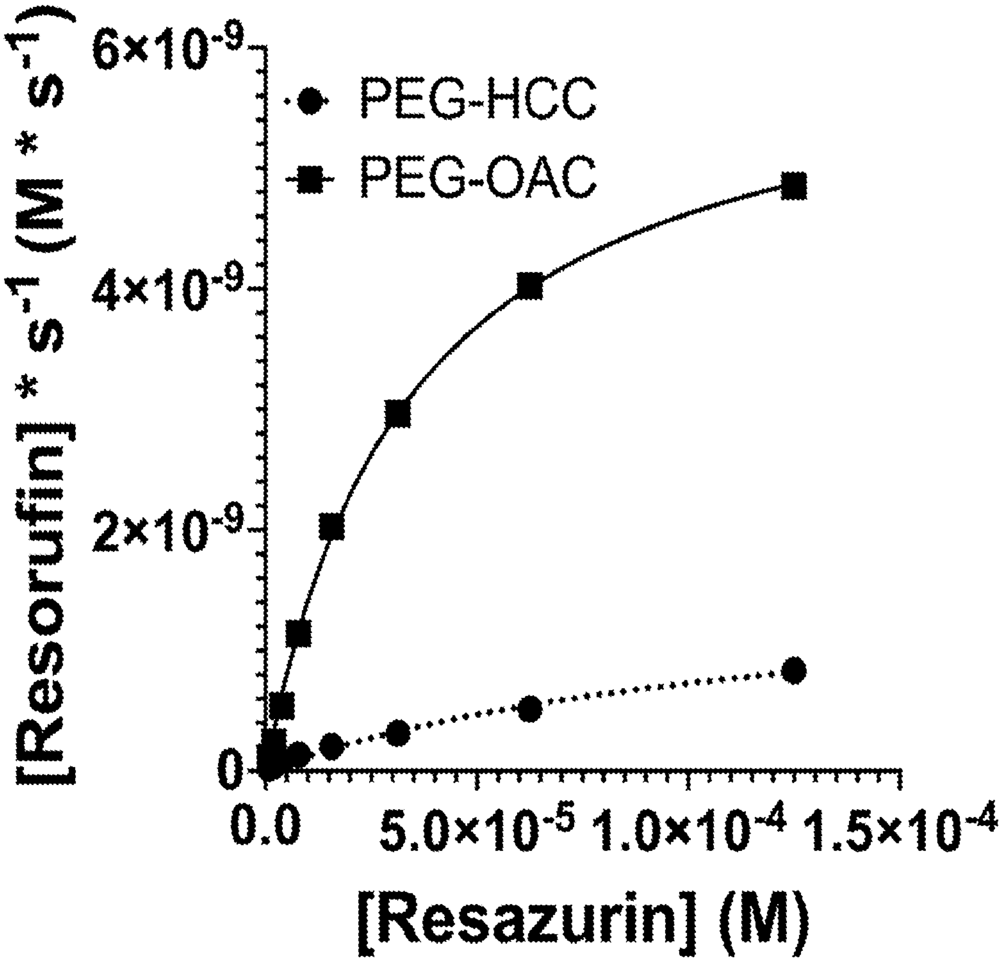
FIG. 12 is a graph showing the reduction of resorufin by dithiothreitol in the presence of PEG-HCCs or PEG-OACs.

All of these skeletons can be modified with unique R groups that can facilitate conjugation to linker molecules or nanoparticles. Importantly, small molecules such as dithiothreitol (FIGS. 9A and 12) and glutathione (FIG. 9B) can reach the surface of the particles despite heavy PEGylation, a property necessary for the use of a thiolytic $H_2S$ donor.

BIBLIOGRAPHY

The following publications are specifically incorporated herein by reference in their entirety. Citation or identification of any document in this application is not an admission that such document is available as prior art to the present invention.

1. Cornelius, C. et al., *Antioxid Redox Signal.* 2013; 19(8): 836-853. Epub 2013 Apr. 4. doi: 10.1089/ars.2012.4981. PubMed PMID: 23547621.
2. Samuel, E. L., et al. *Trends Biotechnol.* 2014; 32(10): 501-505. Epub 2014 Sep. 2. doi: 10.1016/j.tibtech.2014.08.005. PubMed PMID: 25175886; PMCID: PMC4174960.
3. Kurland, D. et al. *J Neurotrauma.* 2012; 29(1):19-31. Epub 2011 Oct. 13. doi: 10.1089/neu.2011.2122. PubMed PMID: 21988198; PMCID: PMC3253310.
4. Bitner, B. R. et al. *ACS Nano.* 2012; 6(9):8007-8014. Epub 2012 Aug. 8. doi: 10.1021/nn302615f. PubMed PMID: 22866916; PMCID: PMC3458163.
5. Marcano, D. C. et al. *J Neurotrauma.* 2013; 30(9):789-796. Epub 2012 Aug. 30. doi: 10.1089/neu.2011.2301. PubMed PMID: 22928502.
6. Samuel E. L. et al., *Proc Natl Acad Sci USA.* 2015; 112(8):2343-2348. Epub 2015 Feb. 13. doi: 10.1073/pnas.1417047112. PubMed PMID: 25675492; PMCID: PMC4345556.
7. Mendoza, K. et al., *J Neurotrauma.* Epub 2019; 2019 Feb. 2. doi: 10.1089/neu.2018.6027. PubMed PMID: 30704349.
8. Derry, P. J. et al., *Nanoscale.* 2019; 11:10791-10807. Epub 2019 May 28. doi: 10.1039/c9nr00807a. PubMed PMID: 31134256.
9. Freund, A. et al., *Trends Mol Med.* 2010; 16(5):238-246. Epub 2010 May 7. doi: 10.1016/j.molmed.2010.03.003. PubMed PMID: 20444648; PMCID: PMC2879478.
10. Tominaga, T. et al., *PLoS One.* 2019; 14(3):e0213673. Epub 2019 Mar. 12. doi: 10.1371/journal.pone.0213673. PubMed PMID: 30856215; PMCID: PMC6411151.
11. Manea, F. et al., *Angew Chem Int Ed Engl.* 2004; 43(45):6165-6169. Epub 2004 Nov. 19. doi: 10.1002/anie.200460649. PubMed PMID: 15549744.
12. Wei, H. et al., *Chem Soc Rev.* 2013; 42(14):6060-6093. Epub 2013 Jun. 7. doi: 10.1039/c3cs35486e. PubMed PMID: 23740388.
13. Wu, J. et al., *Chem Soc Rev.* 2018; 47(5) 1822-1873. Epub 2018 Dec. 12. PubMed PMID: 30534770.
14. Zhou, F. et al., *Small.* 2011; 7(19):2727-2735. Epub 2011 Aug. 24. doi: 10.1002/smll.201100669. PubMed PMID: 21861293.
15. Mukherjee, S. P. et al., *Nanoscale.* 2018; 10(3):1180-1188. Epub 2017 Dec. 23. doi: 10.1039/c7nr03552g. PubMed PMID: 29271441.
16. Jalilov, A. S. et al., *ACS Appl Mater Interfaces.* 2016; 8(24):15086-15092. Epub 2016 Jun. 2. doi: 10.1021/acsami.6b03502. PubMed PMID: 27245481; PMCID: PMC4920082.
17. Nilewski, L. et al., *ACS Appl Mater Interfaces.* 2019; 11(18):16815-16821. Epub 2019 Apr. 18. doi: 10.1021/acsami.9b01082. PubMed PMID: 30995006.
18. Tatlisumak, T. et al., *Nat Rev Neurol.* 2018; 14(4):237-2250. Epub 2018 Mar. 10. doi: 10.1038/nrneurol.2018.17. PubMed PMID: 29521335.
19. Daglas, M. et al., *Front Neurosci.* 2018; 12: Article 981. Epub 2019 Jan. 9. doi: 10.3389/fnins.2018.00981. PubMed PMID: 30618597; PMCID: PMC6306469.
20. Xi, G. et al., *Prog Neurobiol.* 2014; 115:45-63. Epub 2013 Oct. 22. doi: 10.1016/j.pneurobio.2013.09.007. PubMed PMID: 24139872; PMCID: PMC3961535.
21. Aft, R. L. et al., *J Biol Chem.* 1983; 258(19):12069-12072.
22. Fielder, E. et al., *J Alzheimers Dis.* 2017; 60:107-131. doi: 10.3233/JAD-161221.
23. Ritzel, R. M. et al. *Neurobiol Aging.* 2019; 77:194-206. Epub 2019 Mar. 25. doi: 10.1016/j.neurobiolaging.2019.02.010. PubMed PMID: 30904769; PMCID: PMC6486858.

24. Masaldan, S. et al. *Redox Biol.* 2018; 14:100-115. Epub 2017 Sep. 10. doi: 10.1016/j.redox.2017.08.015. PubMed PMID: 28888202; PMCID: PMC5596264.
25. Doll, S. et al., *IUBMB Life.* 2017; 69(6):423-434. Epub 2017 Mar. 10. doi: 10.1002/iub.1616. PubMed PMID: 28276141.
26. Zille, M. et al., *Stroke.* 2017; 48(4):1033-1043. Epub 2017 Mar. 3. doi: 10.1161/STROKEAHA.116.015609. PubMed PMID: 28250197; PMCID: PMC5613764.
27. Ye, R., et al., *Nat Commun.* 2013; 4: Article 2943. Epub 2013 Dec. 7. doi: 10.1038/ncomms3943. PubMed PMID: 24309588.
28. Ye, R. et al., *ACS Appl Mater Interfaces.* 2015; 7(12): 7041-7048. Epub 2015 Mar. 12. doi: 10.1021/acsami.5b01419. PubMed PMID: 25757413.
29. Service Ea. Powdered Activated Charcoal—Medical Grade Coconut Shell—EnviroSupply & Service 2019 [cited 2019 Jul. 18, 2019].
30. Shilo, M. *J Nanobiotechnol.* 2015; 13: Article 19. Epub 2015 Apr. 17. doi: 10.1186/s12951-015-0075-7. PubMed PMID: 25880565; PMCID: PMC4359781.
31. Chua, C. K. et al., *Chemistry.* 2015; 21(36):12550-12562. Epub 2015 Jul. 2. doi: 10.1002/chem.201501383. PubMed PMID: 26126767.
32. Chua, C. K. et al., *Chemistry.* 2014; 20(48):15760-15767. Epub 2014 Oct. 7. doi: 10.1002/chem.201404205. PubMed PMID: 25284355.
33. Mukherjee, S. P. et al., *PLoS One.* 2016; 11(11): e0166816. Epub 2016 Nov. 24. doi: 10.1371/journal-.pone.0166816. PubMed PMID: 27880838; PMCID: PMC5120825.
34. Faria, M. et al., *Nat Nanotechnol.* 2018; 13(9):777-785. Epub 2018 Sep. 8. doi: 10.1038/s41565-018-0246-4. PubMed PMID: 30190620; PMCID: PMC6150419.
35. Berlin, J. M. et al., *ACS Nano.* 2010; 4(8):4621-4636. Epub 2010 Aug. 5. doi: 10.1021/nn100975c. PubMed PMID: 20681596; PMCID: PMC2935702.
36. Cheng, G. et al., *Br J Pharmacol.* 2012; 167(4):699-719. Epub 2012 Sep. 26. doi: 10.1111/j.1476-5381.2012.02025.x. PubMed PMID: 23003569; PMCID: PMC3575772.
37. Fischer, T. D., *Front Syst Neurosci.* 2016; 10: Article 29. Epub 2016 Apr. 12. doi: 10.3389/fnsys.2016.00029. PubMed PMID: 27065821; PMCID: PMC4811888.
38. Hiebert, J. B. et al., *Am J Med Sci.* 2015; 350(2):132-138.
39. Lee, J. Y. et al., *J Cereb Blood Flow Metab.* 2010; 30(11):1793-1803. Epub 2010 Aug. 26. doi: 10.1038/jcbfm.2010.137. PubMed PMID: 20736956; PMCID: PMC2970675.
40. Robinson, S. R. et al., *Redox Rep.* 2009; 14(6):228-235. Epub 2009 Dec. 17. doi: 10.1179/135100009X12525712409931. PubMed PMID: 20003707.
41. Itoh, R. et al., *FEBS Lett.* 2013; 587(14):2131-2136. Epub 2013 Jun. 6. doi: 10.1016/j.febslet.2013.05.036. PubMed PMID: 23735699.
42. Higdon, A. N. et al., *Am J Physiol Heart Circ Physiol.* 2012; 302(7):H1394-409. Epub 2012 Jan. 17. doi: 10.1152/ajpheart.00584.2011. PubMed PMID: 22245770; PMCID: PMC3330785.
43. Technologies A. Agilent Seahorse XF Cell Mito Stress Test Kit. Agilent Technologies; 2019.
44. Sure, V. N. et al., *Geroscience.* 2018; 40(4):365-375. Epub 2018 Aug. 4. doi: 10.1007/s11357-018-0037-8. PubMed PMID: 30074132; PMCID: PMC6136296.
45. Yepez, V. A. et al., *PLoS One.* 2018; 13(7):e0199938. Epub 2018 Jul. 12. doi: 10.1371/journal.pone.0199938. PubMed PMID: 29995917; PMCID: PMC6040740.
46. Keberle, H. *Ann NY Acad Sci.* 1964; 119:758-768.
47. Bentur, Y. et al., *Drug Safety.* 1991; 6(1):37-46.
48. Fabian, R. H. et al., *Front Neurol.* 2018; 9: Article 199. Epub 2018 Apr. 25. doi: 10.3389/fneur.2018.00199. PubMed PMID: 29686642; PMCID: PMC5900022.
49. Lederman, H. M. et al., *Blood.* 1984; 64(3):748-753. Epub 1984 Sep. 1. PubMed PMID: 6380622.
50. Sen, D. et al., *Crit Rev Biochem Mol Biol.* 2011; 46(6):478-492. Epub 2011 Oct. 1. doi: 10.3109/10409238.2011.618220. PubMed PMID: 21958168.
51. Reddy, S. V. et al., *Blood.* 1998; 91(5):1793-1801. Epub 1998 Mar. 21. PubMed PMID: 9473248.
52. Li, W. et al., *Nucleic Acids Res.* 2016; 44(15):7373-7384. Epub 2016 Jul. 17. doi: 10.1093/nar/gkw634. PubMed PMID: 27422869; PMCID: PMC5009756.
53. Golub, E. et al., *Angew Chem* (*Int Ed.* 2011; 50(49): 11710-11714. Epub 2012 Jan. 10. PubMed PMID: 22229160.
54. Travascio, P. et al., *ChemBiol.* 1998; 5(9):505-517. Epub 1998 Sep. 30. PubMed PMID: 9751647.
55. Ghahremani, N. M. et al., *Journal Biol Phys.* 2017; 43(1):5-14. Epub 2016 Oct. 19. doi: 10.1007/s10867-016-9430-7. PubMed PMID: 27752804; PMCID: PMC5323342.
56. Mitra, J. et al., *Proc Natl Acad Sci USA* 2019; 116(10) 4696-4705; Epub 2019 Feb. 17. doi: 10.1073/pnas.1818415116. PubMed PMID: 30770445.
57. Zhu, Y. et al., *Nat Commun.* 2019; 10(1): Article 2313. Epub 2019 May 28. doi: 10.1038/s41467-019-10332-8. PubMed PMID: 31127121; PMCID: PMC6534554.
58. Biernacka, A. et al., *Commun biol.* 2018; 1: Article 181. Epub 2018 Nov. 6. doi: 10.1038/s42003-018-0165-9. PubMed PMID: 30393778; PMCID: PMC6208412.
59. Yeo, N.C. et al., *Nat Methods.* 2018; 15(8):611-616. Epub 2018 Jul. 18. doi: 10.1038/s41592-018-0048-5. PubMed PMID: 30013045; PMCID: PMC6129399.
60. Hasan, R. N. et al., *CircRes.* 2008; 102(1):42-50. Epub 2007 Oct. 31. doi: 10.1161/circresaha.107.155143. PubMed PMID: 17967787.
61. Nonaka, M. et al., *J Neurotrauma.* 1999; 16(11):1023-1031.
62. Gonzalez-Hunt, C. P. et al., *Curr Protoc Toxicol.* 2016; 67:20.11.1-20.11.25. Epub 2016 Feb. 2. doi: 10.1002/0471140856.tx2011s67. PubMed PMID: 26828332; PMCID: PMC4928199.
63. Povlishock, J. T. et al., "The Blood-Brain Barrier in Brain Injury: An Overview.". In: M. Y.-T. G, Dietrich W D, editors. *The Role of Neurotransmitters in Brain Injury* 992.
64. Maynard, M. E. et al., *J Neurotrauma.* 2019; 36(13): 2147-2152. Epub 2019 Jan. 24. doi: 10.1089/neu.2018.6155. PubMed PMID: 30672378; PMCID: PMC6602106.
65. Prins, M. L. et al., *Dev Neurosci.* 2010; 32(5-6):510-518. Epub 2010 Sep. 11. doi: 10.1159/000316800. PubMed PMID: 20829578; PMCID: PMC3215244.
66. Dash, P. K. et al., *PLoS One.* 2011; 6(9):e24648. Epub 2011 Sep. 22. doi: 10.1371/journal.pone.0024648. PubMed PMID: 21935433; PMCID: PMC3174188.
67. Rall, J. M. et al., *Brain Res.* 2003; 968(2):273-276. doi: 10.1016/s0006-8993(03)02248-0.
68. Hylin, M. J. et al., *J Neurotrauma.* 2013; 30(9):702-715. Epub 2013 Jan. 11. doi: 10.1089/neu.2012.2630. PubMed PMID: 23301501; PMCID: PMC3941923.

69. Blum, S. et al., *J Neurosci.* 1999; 19(9):3535-3544.
70. Dixon, E. et al., *J Neurosci Meth.* 1991; 39:253-262.
71. Hood, K. N. et al., *J Neurosci.* 2018; 38(9):2372-2384. Epub 2018 Feb. 2. doi: 10.1523/JNEUROSCI.1756-17.2018. PubMed PMID: 29386258; PMCID: PMC5830522.
72. Dash, P. K. et al., *J Neurotrauma.* 2015; 32(20):1608-1620. Epub 2015 Apr. 7. doi: 10.1089/neu.2014.3772. PubMed PMID: 25843479; PMCID: PMC4593880.
73. Zhao, J. et al., *J Neurotrauma.* 2018; 35(2):362-374. Epub 2017 Nov. 2. doi: 10.1089/neu.2017.5102. PubMed PMID: 29088998; PMCID: PMC5784795.
74. Morris, R. G. M. et al., *Nature.* 1986; 319(27):774-776.
75. Hylin, M. J. et al., *J Neurosci Res.* 2018; 96(3):416-426. Epub 2017 Dec. 13. doi: 10.1002/jnr.24121. PubMed PMID: 29230855; PMCID: PMC6425965.
76. Dash, P. K. et al., *AN. Neurosci Lett.* 2009; 460(2):103-107. Epub 2009 Jun. 12. doi: 10.1016/j.neulet.2009.04.028. PubMed PMID: 19515491; PMCID: PMC2700200.
77. Hurt. R. H. et al., *Carbon* 2006; 44, 1028-1033.
78. Sayes, C. M. et al. 2006. *Toxicol. Lett.* 2006; 161, 135-142.
79. Schipper, M. L. et al. *Nat Nanotechnol* 2008; 3, 216-221.
80. U.S. Pat. No. 9,572,834—Tour et al.
81. Chauvin, J. R et al., *Chem Sci* 2019; 10, 4999-5010.
82. Jalilov, A. S. et al., *ACS Appl Mater Interfaces* 2016; 8, 15086-15092.
83. Olson, K. R. et al., *Free Radic Biol Med* 2019; 135, 1-14.
84. Olson, K. R. et al. *Redox Biol* 2018; 15, 74-85.
85. Samuel, E. L. et al., *Proc Natl Acad Sci USA* 2015; 112, 2343-2348.
86. Dharmalingam, P. et al., *ACS Nano* 2020; 14, 2827-2846.
87. Olson, K. R. et al., *Redox Biol* 2018; 15, 74-85.
88. Fujii, S. et al., *Br J Pharmacol* 2019; 176(4) 607-615.
89. Kolluru, G. K. et al., *Arterioscler Thromb Vasc Biol* 2020; 40(4), 874-884.
90. Cuevasanta, E. et al., *Arch Biochem Biophys* 2017; 617 9-25.
91. Olson, K. R., et al., *Redox Biol* 2017; 12 325-339.
92. Filipovic, M. R. et al., *Chem Rev* 2018; 118(3), 1253-1337.

The invention claimed is:

1. Oxidized-carbon nanoparticles prepared by a process that comprises contacting one or more carbon nanoparticulate materials with concentrated nitric acid or fuming nitric acid, optionally dissolved in concentrated sulfuric acid or fuming sulfuric acid, to form a population of oxidized-carbon nanoparticles;

wherein the one or more carbon nanoparticulate materials are selected from the group consisting of graphene, graphene nanoribbons, graphene oxide, graphite, graphite oxide nanoribbons, carbon black, hydrophilic carbon clusters, coal, activated coal and activated charcoal;

wherein the oxidized-carbon nanoparticles form a dispersion in water in the absence of an exogenously-supplied functionalized solubilizing agent and form a non-settling dispersion in water at a concentration of about 1 to about 5 mg/mL, said dispersion being stable to settling at ambient room temperature for at least seven days and exhibiting an absorbance maximum at about 220 nm, said oxidized-carbon nanoparticles being generally discoid particles and wherein said particles have diameters of about 5 to about 30 nm and thicknesses of about 0.3 to about 2 nm, containing about 9 to about 15 percent carbonyl groups by X-ray photoelectron spectroscopy (XPS), and passing through a 0.22 μm pore size polyethersulfone (PES) filter membrane.

2. The oxidized-carbon nanoparticles according to claim 1 that exhibit a reduction potential with an onset above about 0.05 V and a reduction maximum at about −2 V as measured by cyclic voltammetry (CV).

3. A method of forming persulfide and/or polysulfide from hydrogen sulfide that comprises contacting cells in need of protein persulfidation with an effective amount of the oxidized-carbon nanoparticles of claim 1.

4. The method according to claim 3, wherein:

(i) said persulfide and/or polysulfide is prepared from endogenously or exogenously released hydrogen sulfide; and/or (ii) said contacting is repeated a plurality of times.

5. The method according to claim 3, wherein said oxidized-carbon nanoparticles are functionalized with one or more exogenously-supplied specific substituents that are selected from the group of a hydrogen sulfide-releasing moiety, a solubilizing agent, a biological barrier transporter moiety, a tissue-targeting agent, an assay-identifying agent, a chelating agent and a pharmaceutical agent.

6. The method according to claim 5, wherein said oxidized-carbon nanoparticles are functionalized:

(i) with a solubilizing agent selected from one or more of the group consisting of poly(ethylene glycol) [PEG], poly(propylene glycol) [PPG], poly(ethyleneimine) [PEI], poly(vinyl alcohol) [PVA], PPG-PEG block copolymers, $C_{12}$-$C_{18}$-poly(ethyleneoxide)ether and poly (acrylic acid) [PAA];

(ii) with an exogenously-provided hydrogen sulfide-releasing moiety that provides hydrogen sulfide by thiolysis, or enzymolysis, wherein said hydrogen sulfide-releasing moiety is selected from one or more of the group consisting of a N-benzoylthiolbenzamide, an acyl perthiol, an aryl thioamide, a dithioperoxyanhydride, an S-aroylthiox-amine, a geminal-dithiol, and a trimethyl lock prodrug;

(iii) with a transporter moiety that is selected from one or more of the group consisting of adamantanyl, amantadinyl, memantinyl, rimantadinyl, dopamantinyl, tromantadinyl, vildagliptinyl and karmantadinyl groups; and/or (iv) with a pharmaceutical agent that is selected from one or more of the group consisting of cannabigerol, cannabigerol monomethyl ether, cannabinerolic acid A, cannabigerovarin, cannabigerolic acid A, cannabigerolic acid A monomethyl ether, cannabigerovarinic acid A, cannabichromene, cannabichromenic acid A, cannabivarichromene, cannabichromevarin, cannabichromevarinic acid A, cannabidiol, cannabidiorcol, cannabidiolic acid, cannabidivarinic acid, cannabinodiol, cannabinodivarin, cannabivarin, cannabicitran, HU-210, and dexanabinol.

7. A pharmaceutical composition that comprises oxidized-carbon nanoparticles according to claim 1 that is present in a persulfide- and/or polysulfide-producing effective amount of dispersed in water.

8. The pharmaceutical composition according to claim 7, wherein said pharmaceutically acceptable composition is an aqueous composition adapted for parenteral administration, wherein said pharmaceutically acceptable composition has an osmolality that is isotonic with the blood of an intended recipient, further wherein said osmolality is about 275 to about 295 mOsm/kg.

9. A method of preparing an aqueous composition of oxidized-carbon nanoparticles of claim 1 comprising the steps of:

a) admixing one or more carbon nanoparticulate materials in an oxidizing effective amount of one or more of concentrated nitric acid or fuming nitric acid alone or dissolved in concentrated sulfuric acid or fuming sulfuric acid to form an acidic reaction composition;

b) stirring said acidic reaction composition at atmospheric pressure at a temperature of about 22° C. and reflux for a time sufficient to form oxidized-carbon nanoparticles that contain about 9 to about 15 percent carbonyl groups by X-ray photoelectron spectroscopy (XPS);

c) cooling said acidic refluxed reaction composition and quenching same in an aqueous medium that also optionally includes a base to form an aqueous reacted composition;

d) dialyzing the aqueous reacted composition through a membrane with a molecular weight cut off of about 1000 Da against water for a time sufficient to remove water-soluble materials of a molecular weight of less than about 1000 Da to form an aqueous composition of oxidized-carbon nanoparticles; and e) filtering said aqueous composition of oxidized-carbon nanoparticles through a 0.22 μm pore size polyethersulfone (PES) filter membrane to form an aqueous composition filtrate of said oxidized-carbon nanoparticles.

10. The method of preparation according to claim 9 further including the step of separating the water and oxidized-carbon nanoparticles, and collecting the oxidized-carbon nanoparticles.

11. The method according to claim 4, wherein said oxidized-carbon nanoparticles are prepared from activated charcoal.

12. The oxidized carbon nanoparticles of claim 1 for use in medicine, wherein the use is in a method of forming persulfide and/or polysulfide from hydrogen sulfide that comprises contacting cells in need of protein persulfidation in vivo with an effective amount of the oxidized-carbon nanoparticles.

13. The oxidized-carbon nanoparticles for use according to claim 12, wherein:

(i) said persulfide and/or polysulfide is prepared from endogenously or exogenously released hydrogen sulfide; and/or (ii) said contacting is repeated a plurality of times.

14. The oxidized-carbon nanoparticles for use according to claim 12, wherein said oxidized-carbon nanoparticles are functionalized with one or more exogenously-supplied specific substituents that are selected from the group of a hydrogen sulfide-releasing moiety, a solubilizing agent, a biological barrier transporter moiety, a tissue-targeting agent, an assay-identifying agent, a chelating agent and a pharmaceutical agent.

15. The oxidized-carbon nanoparticles for use according to claim 14, wherein said oxidized-carbon nanoparticles are functionalized with:

(i) a solubilizing agent selected from one or more of the group consisting of poly(ethylene glycol) [PEG], poly (propylene glycol) [PPG], poly(ethyleneimine) [PEI], poly(vinyl alcohol) [PVA], PPG-PEG block co-polymers, $C_{12}$-$C_{18}$-poly(ethyleneoxide)ether and poly (acrylic acid) [PAA];

(ii) with an exogenously-provided hydrogen sulfide-releasing moiety that provides hydrogen sulfide by thiolysis, or enzymolysis, wherein said hydrogen sulfide-releasing moiety is selected from one or more of the group consisting of a N-benzoylthiolbenzamide, an acyl perthiol, an aryl thioamide, a dithioperoxyanhydride, an S-aroylthiox-amine, a geminal-dithiol, and a trimethyl lock prodrug; (iii) with a transporter moiety that is selected from one or more of the group consisting of adamantanyl, amantadinyl, memantinyl, rimantadinyl, dopamantinyl, tromantadinyl, vildagliptinyl and karmantadinyl groups; and/or (iii) with a pharmaceutical agent that is selected from one or more of the group consisting of cannabigerol, cannabigerol monomethyl ether, cannabinerolic acid A, cannabigerovarin, cannabigerolic acid A, cannabigerolic acid A monomethyl ether, cannabigerovarinic acid A, cannabichromene, cannabichromenic acid A, cannabivarichromene, cannabichromevarin, cannabichromevarinic acid A, cannabidiol, cannabidiorcol, cannabidiolic acid, cannabidivarinic acid, cannabinodiol, cannabinodivarin, cannabivarin, cannabicitran, HU-210, and dexanabinol.

16. A method of forming persulfide and/or polysulfide from hydrogen sulfide that comprises contacting cells in need of protein persulfidation with a pharmaceutical composition comprising the oxidized-carbon nanoparticles of claim 1, wherein the oxidized-carbon nanoparticles are present in the pharmaceutical composition at a concentration of from about 0.1 to about 10 m/L.

17. The oxidized-carbon nanoparticles according to claim 1 that are free from an exogenously-supplied functionalized solubilizing agent.

* * * * *